(12) United States Patent
Brasier et al.

(10) Patent No.: US 10,168,337 B2
(45) Date of Patent: Jan. 1, 2019

(54) METHOD AND BIOMARKERS FOR THE DETECTION OF DENGUE HEMORRHAGIC FEVER

(75) Inventors: Allan Brasier, Galveston, TX (US); Adrian Recinos, Galveston, TX (US); John E. Wiktorowicz, League City, TX (US); Heidi Spratt, Galveston, TX (US); Hyunsu Ju, League City, TX (US); Nikos Vasilakis, Galveston, TX (US); Ernesto E. T. Marquez, Pittsburgh, PA (US); Marli Tenorio, Recife (BR); Laura H. V. G. Gil, Recife (BR); Eduardo Nascimento, Allentown, PA (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 669 days.

(21) Appl. No.: 14/124,343

(22) PCT Filed: Jun. 6, 2012

(86) PCT No.: PCT/US2012/041131
§ 371 (c)(1),
(2), (4) Date: Aug. 20, 2015

(87) PCT Pub. No.: WO2012/170556
PCT Pub. Date: Dec. 13, 2012

(65) Prior Publication Data
US 2016/0003845 A1    Jan. 7, 2016

Related U.S. Application Data

(60) Provisional application No. 61/493,923, filed on Jun. 6, 2011.

(51) Int. Cl.
*G01N 33/68*    (2006.01)
*G01N 33/564*    (2006.01)
*G01N 33/569*    (2006.01)

(52) U.S. Cl.
CPC ....... *G01N 33/6869* (2013.01); *G01N 33/564* (2013.01); *G01N 33/56983* (2013.01); *G01N 33/6851* (2013.01); *G01N 2333/185* (2013.01); *G01N 2333/47* (2013.01); *G01N 2333/4716* (2013.01); *G01N 2333/5428* (2013.01); *G01N 2333/55* (2013.01); *G01N 2333/76* (2013.01); *G01N 2800/26* (2013.01); *Y02A 50/53* (2018.01)

(58) Field of Classification Search
None
See application file for complete search history.

(56) References Cited

FOREIGN PATENT DOCUMENTS

WO    WO 2010/043973    4/2010
WO    WO 2012/170556    12/2013

OTHER PUBLICATIONS

York et al., Statistics in Medicine, 2006, 25:1355-1367.*
Albuquerque et al. Two-Dimensional Difference Gel Electrophoresis (DiGE) Analysis of Plasmas from Dengue Fever Patients. J. Proteome Res. 8, 5431-5441 (2009).
Bozza et al. Multiplex cytokine profile from dengue patients: MIP-1beta and IFN-gamma as predictive factors for severity. BMC Infectious Diseases. 8(86), PDF pp. 1-12. (2008).
Brasier et al. Discovery proteomics and nonparametric modeling pipeline in development of a candidate biomarder panel for dengue hemorrhagic fever. Clinical and Translational Science 5(1), 8-20 (2010).
Brasier et al. A three-component biomarker panel for prediction of dengue hemorrhagic fever. Am. J. Trop. Med. Hyg. 86(2), 341-348 (2012).
Chareonsirisuthigul et al. Dengue virus (DENV) antibody-dependent enhancement of infection upregulates the production of anti-inflammatory cytokines, but suppresses anti-DENV free radical and pro-inflammatory cytokine production, in THP-1 cells. J. Gen. Virol. 88, 365-375 (2007).
Chaturvedi et al. Cytokine cascade in dengue hemorrhagic fever: implications for pathogenesis. FEMS Immunology and Medical Microbiology 28, 183-188 (2000).
Cook et al. Tree and spline based association analysis of gene-gene interaction models for ischemic stroke. Stat. Med. 23, 1439-1453 (2004).
Dowsey et al. Informatics and statistics for analyzing 2-d gel electrophoresis images. Methods Mol. Biol. 604, 239-255 (2010).
Endy et al. Relationship of Preexisting Dengue Virus (DV) Neutralizing Antibody Levels to Viremia and Severity of Disease in a Prospective Cohort Study of DV Infection in Thailand. J. Infect. Dis. 189, 990-1000 (2004).
Fawcett et al. An introduction to ROC analysis. Pattern Recognition Letters 27, 861-874 (2006).
Friedman. Multivariate Adaptive Regression Splines. Annals of Statistics 19,1-67 (1991).
Gilbert. Dissertation. In Search of Novel Dengue Biomarkers Using SELDI-TOF MS and Other Proteomic Technologies. A thesis submitted in partial fulfillment of the requirements for the degree of Master of Science in Experimental Medicine in the University of McGill University, Sep. 2010.
Graham et al. A prospective seroepidemiologic study on dengue in children four to nine years of age in Yogyakarta, Indonesia I. Studies in 1995-1996. Am. J. Trop. Med. Hyg. 61, 412-419 (1999).

(Continued)

*Primary Examiner* — Nicole Kinsey White
(74) *Attorney, Agent, or Firm* — Norton Rose Fulbright US LLP

(57) ABSTRACT

The present invention provides compositions and methods for detecting, analyzing, and identifying biomolecules used to diagnose patient with risk of DHF. More particularly, the invention provides plasma biomarkers including complement factor D to complement factor H (FactorD/FactorH) ratio and levels of one or more of IL2, desmoplakin, and high molecular weight albumin, which are used to detect risk of developing DHF.

2 Claims, 13 Drawing Sheets

(56) References Cited

OTHER PUBLICATIONS

Green, S., A. Rothman. Immunopathological mechanisms in dengue and dengue hemorrhagic fever. Curr. Opin. Infec. Dis. 19, 429-436 (2006).
Guzman et al. Effect of age on outcome of secondary dengue 2 infections. Int. J. Infect. Dis. 6,118-124 (2002).
Guzman, M., G. Kouri. Dengue: an update. Lancet Infect Dis. 2(1), 33-42 (2002).
International Search Report, PCT/US2012/0411131, dated Aug. 27, 2012.
Jamaluddin et al. Role of Peroxiredoxin-1 and -4 in Protection of RSV-induced Cysteinyl-oxidation of Nuclear Cytoskeletal Proteins. J. Virol. 84, 9533-9545 (2010).
Karp et al. Comparison of DIGE and post-stained gel electrophoresis with both traditional and SameSpots analysis for quantitative proteomics. Proteomics 8, 948-960 (2008).
Kliks et al. Antibody-dependent enhancement of dengue virus growth in human monocytes as a risk factor for dengue hemorrhagic fever. Am. J. Trop. Med. Hyg. 40(4), 444-51 (1989).
Martina et al. Dengue Virus Pathogenesis: an Integrated View. Clin. Microbiol. Rev. 22, 564-581 (2009).
Miseta, A., P. Csutora Relationship between the occurrence of cysteine in proteins and the complexity of organisms. Molecular Biology of Evolution 17(8), 1232-1239 (2000).
Nascimento et al. Alternative Complement Pathway Deregulation is Correlated with Dengue Severity. PLoS ONE vol. 4 (5), 1-13 (2009).
Nasirudeen et al. Gene Expression Profiling by Microarray Analysis Reveals an Important Role for Caspase-1 in Dengue Virus-Induced p53-Mediated Apoptosis. J. Med. Virol. 81, 1069-1081 (2009).
Oishi et al. Correlation between increased platelet-associated IgG and thrombocytopenia in secondary dengue virus infections. J. Med. Virol. 71, 259-64 (2003).
Perez et al. IL-10 levels in Dengue patients: some findings from the exceptional epidemiological conditions in Cuba. J. Med. Viral. 73, 230-234 (2004).
Pretzer, E., J. Wiktorowicz. Saturation fluorescence labeling of proteins for proteomic analyses. Anal. Biochem. 374, 250-262 (2008).
Rifai, N., R. Gertzen. Biomarker Discovery and Validation. Clinical Chemistry 52(9), 1635-1637 (2006).
Srichaikul et al. Fibrinogen Metabolism and Disseminated Intravascular Coagulation in Dengue Hemorrhagic Fever. Am. J. Trop. Med. Hyg. 26(3), 525-532 (1977).
Stephenson, J. R. Understanding dengue pathogenesis: implications for vaccine design. Bulletin of World Health Organization 83, 308-14 (2005).
Thayan et al. The use of two-dimension electrophoresis to identify serum biomarkers from patients with dengue haemorrhagic fever. Trans. R. Soc. Trop. Med. Hyg. 103, 413-419 (2009).
Thomas et al. Influence of the dengue serotype, previous dengue infection, and plasma viral load on clinical presentation and outcome during a dengue-2 and dengue-4 co-epidemic. Am. J. Trop. Med. Hyg. 78(6), 990-998 (2008).
Villar-Centeno et al. Biochemical Alterations as Markers of Dengue Hemorrhagic Fever. Am. J. Trop. Med. Hyg. 78(3), 370-374 (2008).
Zhang, W., B. Chait. ProFound: An Expert System for Protein Identification Using Mass Spectrometric Peptide Mapping Information. Anal. Chem. 72, 2482-2489 (2000).

\* cited by examiner

METHOD AND BIOMARKERS FOR THE DETECTION OF DENGUE HEMORRHAGIC FEVER

This Application claims priority to and is a U.S. national stage filing of PCT application number PCT/US2012/041131, and claims priority to U.S. Provisional Patent Application No. 61/493,923 filed Jun. 6, 2011, each of which is incorporated herein by reference in its entirety.

STATEMENT REGARDING FEDERALLY FUNDED RESEARCH

This invention was made with government support under HHSN272200800048C awarded by the National Institutes of Health/National Institute of Allergy and Infectious Diseases. The government has certain rights in the invention.

BACKGROUND

Dengue virus (DENV) infection remains an international public health problem affecting urban populations in tropical and sub-tropical regions, where it is currently estimated that about 2.5 billion people are at risk. Dengue virus is a single positive-stranded RNA virus of the family Flaviviridae, genus *Flavivirus*, which is transmitted among humans primarily by *Aedes aegypti* mosquitoes. In humans, dengue infection can produce diseases of a wide spectrum of severity, ranging from asymptomatic to flu-like dengue fever (DF), and life-threatening dengue hemorrhagic fever (DHF) (Martina et al. *Clin. Microbiol. Rev.* 22:564-81, 2009) or dengue shock syndrome (DSS). DHF is particularly associated with capillary leakage, hemorrhage, circulatory shock, and consequently increased mortality.

Due to a number of factors, including increasing urbanization and globalization of travel, dengue disease is re-emerging in the Americas (Pinheiro and Corber, *World Health Stat. Q.* 50:161-69, 1997). The mortality of DHF is age-dependent, primarily affecting both children and the elderly (Guzman et al., *Int. J Infect. Dis* 6:118-24, 2002). In Southeast Asia, a disproportionate amount of DHF hospitalizations are of children whereas in the Americas, there is a more even distribution across ages.

While DHF fatality rates can exceed 20%, early and intensive supportive therapy has reduced it to less than 1% (Ranjit et al., Aggressive management of dengue shock syndrome may decrease mortality rate: A suggested protocol. *Pediatric Critical Care Medicine* 6:6, 2005). Therefore, early detection and differentiations of dengue disease types can be used for the prognosis and treatment of patients presenting with dengue-like symptoms. Additional methods and combinations of biomarkers to identify DHF are needed.

SUMMARY

Dengue fever is a widespread mosquito born illness that can affect up to ⅗ of the worlds population in the tropics and subtropical regions. A secondary infection is one of the risk factors for development of Dengue Hemorrhagic Fever (DHF). The initial clinical presentation of the two diseases (DF and DHF) are difficult for the clinician to distinguish, however the distinction is important because DHF has a mortality of up to 20%; this mortality can be reduced by intensive supportive care. Accurate early detection of people at risk of DHF can be used to more effectively utilize clinical resources. Combinations of proteins, cytokines and complement factors that can be used in predictive models accurately identify DHF and identify those subjects in need of supportive care.

Certain embodiments are directed to methods for treating Dengue Hemorrhagic Fever (DHF) in a subject comprising treating a Dengue infected individual for DHF when measurement of biomarkers in a sample from the subject detect a ratio of complement factor D to complement factor H (FactorD/FactorH) and increased levels of one or more of IL2, desmoplakin, and high molecular weight albumin (i.e., includes the cross-linked isoforms of albumin, e.g., those having a molecular weight of greater than 200 kDa, which includes both albumin*2 and albumin*3 (MW~263 kDa), but not albumin*1 (MW=52 kDa)) levels to be indicative of DHF. In certain aspects, the measurements are relative to known levels in non-DHF patients. In certain aspects the sample is a serum sample. In a further aspect, the FactorD/FactorH ratio and level of high molecular weight albumin are indicative of DHF. In still a further aspect, the FactorD/FactorH ratio and level of desmoplakin are indicative of DHF. In certain aspects, the FactorD/FactorH ratio and level of high molecular weight albumin, and desmoplakin are indicative of DHF. In a further aspect, the FactorD/FactorH ratio and level of high molecular weight albumin, desmoplakin, and IL2 are indicative of DHF. In certain embodiments the biomarkers are modeled using MARS analysis. In certain aspects, a subject is identified as having DHF with an accuracy of at least or about 70%, 75%, 80%, 85%, 90%, or 95%.

Certain embodiments are directed to methods of identifying a subject at risk of Dengue Hemorrhagic Fever (DHF) comprising measuring biomarkers in a sample from the subject and determining a ratio of complement factor D to complement factor H (FactorD/FactorH) and increased levels of one or more of IL2, desmoplakin, and high molecular weight albumin levels relative to standard.

In certain aspects a MARS model determines DF and DHF with the following accuracies: (A) D/H, hMW albumin, and desmoplakin the prediction success: DF 83.33% correct and DHF 95.45% correct. (B) D/H, hMW albumin, desmoplakin, and IL2 the prediction success: DF 100% correct and DHF 90.1% correct. (C) D/H and hMW albumin prediction success: DF 96.67% correct and DHF 72.73% correct. (D) D/H and desmoplakin prediction success: DF 96.67% correct and DHF 72.73% correct. (E) D/H and IL2 prediction success: DF 100% correct and DHF 36.36% correct (F) D/H prediction success: DF 100% correct and DHF 40.91% correct.

In certain aspects, methods of the invention can further comprise detecting dengue virus infection using PCR or immunoassays (e.g., NS1 detection, IgM ELISA, etc.) for the presence of dengue virus (DENV). The initial diagnosis of dengue infection can then be followed by measuring a set of biomarkers whose levels are indicative for progression to dengue hemorrhagic fever.

A further aspect is directed to a biomarker panel for identifying subjects at risk for DHF. A predictive model can consist of measured levels of cytokines, complement factors and plasma proteins that when combined in nonparametric modeling (multivariate adaptive regression splines) indicates risk for DHF. In certain aspects the biomarkers include two or more of the ratio of FactorD/FactorH, desmoplakin, IL2, and high molecular weight albumin.

Certain embodiments are directed to methods of determining risk of developing Dengue Hemorrhagic Fever (DHF) in individuals infected with dengue virus. The methods include measuring biomarkers including FactorD/FactorH, desmoplakin, IL2, and high molecular weight albumin. In certain aspects the biomarkers are measured in plasma. In various configurations, the methods comprise determining the presence, absence, or quantity of these biomarkers in the plasma of an individual having symptoms of dengue disease. In various aspects, an individual is considered to be at risk of developing DHF if these biomarkers are detected.

In one embodiment, a health care provider, such as a medical doctor, can make a decision on whether to treat the individual, and which modalities of treatment to use, on the basis of the subject individual's profile of biomarkers including FactorD/FactorH, desmoplakin, IL2, and hMW albumin.

Certain embodiments are directed to kits comprising components to be used to measure biomarkers indicative of DHF or to assess risk of developing DHF. In certain aspects, a kit comprises a set of capture reagents for one or more biomarker. In certain aspects the kit can comprise a set of detection reagents for identifying or quantitating biomarkers in a sample. A capture reagent can be an antibody, an aptamer, a kinase, an avimer, or a combination thereof that specifically binds a biomarker. A detection reagent can further comprise a label or other means of quantitating or detecting the presence of a biomarker. The detection reagent can directly or indirectly bind a biomarker or a capture reagent. A detection reagent can be coupled to a label, such as a chromophore, a fluorophore, a hapten (e.g., biotin or digoxygenin), an enzyme, or the various other detectable moities. In certain aspects, an enzyme can be horseradish peroxidase, alkaline phosphatase, chloramphenicol acetyltransferase, or luciferase. In various embodiments, a kit can further comprise a substrate for the enzyme.

As used herein, "a capture reagent" refers to any agent that is capable of binding to an analyte. Preferably, "a capture reagent" refers to any agent that is capable of specifically binding to an analyte, i.e., having a higher binding affinity and/or specificity to the analyte than to any other moiety. Any moiety, such as a cell, a cellular organelle, an inorganic molecule, an organic molecule and a mixture or complex thereof can be used as a capture reagent so long that it has the desired binding affinity and/or specificity to the analyte. The capture reagent can be peptides, proteins (e.g., antibodies or receptors), oligonucleotides, nucleic acids, vitamins, oligosaccharides, carbohydrates, lipids, small molecules, or a complex thereof. Analyte includes proteins, such as complement factors, cytokines and serum proteins.

As used herein, "a detection reagent" refers to any agent that is capable of specifically binding to an analyte and is directly or indirectly coupled with a detectable label. The detection reagent can be peptides, proteins (e.g., antibodies or receptors), oligonucleotides, nucleic acids, vitamins, oligosaccharides, carbohydrates, lipids, small molecules, or a complex thereof.

In certain aspects, treatments for DHF include, but are not limited to transfusion of fresh blood or platelets to correct blooding, giving intravenous (IV) fluids and electrolytes to correct electrolyte imbalances and dehydration, and oxygen therapy to treat low blood oxygen.

As used herein, the term "antigen" is a molecule capable of being bound by an antibody or T-cell receptor. The structural aspect of an antigen, e.g., three-dimensional conformation or modification (e.g., phosphorylation), giving rise to a biological response is referred to herein as an "antigenic determinant" or "epitope." Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In certain embodiments, binding moieties other than antibodies and be engineered to specifically bind to an antigen, e.g., aptamers, avimers, and the like.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains, Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibodies. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin Exp Immunol* 79:315-21, 1990; Kostelny et al., *J. Immunol.* 148:1547-53, 1992.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized).

Moieties of the invention, such as polypeptides, peptides, antigens, capture reagents (capture agents), or detection reagents (detection agents), may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1A:
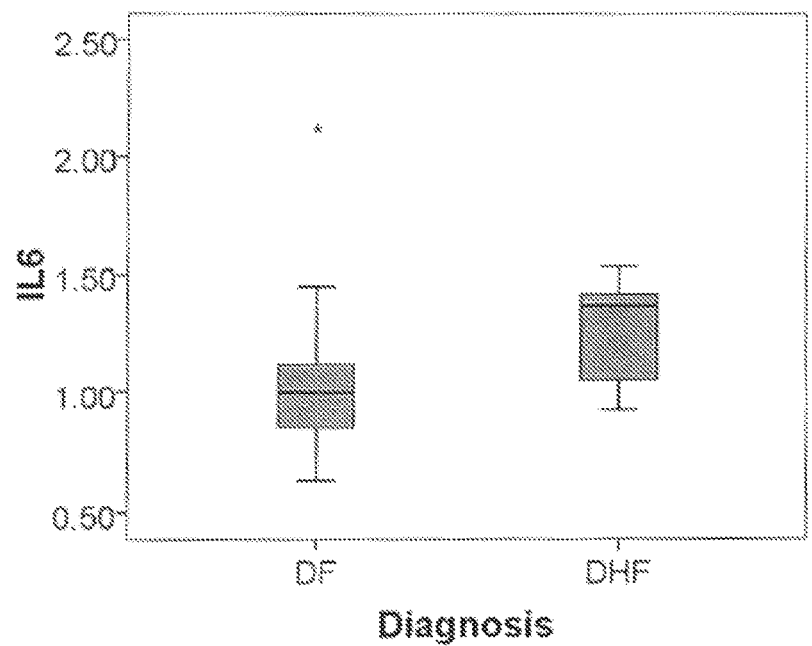
FIGS. 1A-1B. Differential cytokine expression in dengue fever. Shown is a boxplot comparison of log 2-transformed cytokine values for IL-6 (FIG. 1A), and IL-10 (FIG. 1B) by diagnosis. DF, dengue fever; DHF, dengue hemorrhagic fever. Horizontal bar, median value; shaded box, 25-75% interquartile range (IQR); error bars, median±1.5(IQR); *, outlier.

Dengue virus (DENV) belongs to the Family Flaviviridae, genus *flavivirus* that also includes yellow fever (YFV), West Nile (WNV), tick-borne encephalitis (TBEV), and Japanese encephalitis (JEV) viruses. There are 4 primary dengue serotypes that exist which can cause different degrees of disease severity ranging from asymptomatic infections, dengue fever (DF), dengue hemorrhagic fever (DHF), or dengue shock syndrome (DSS).

DENV has an icosahedral core of 40-50 nm in diameter, containing one of the 3 structural proteins, the C protein. It encapsulates the approximately 10,700 nucleotide plus-sense RNA genome. Surrounding the core is a smooth lipid bilayer composed of the other 2 structural proteins, the membrane (prM/M) protein, and the envelope glycoprotein (E) (Kuhn et al., *Cell* 108:717-25, 2002).

DENV also encodes 7 non-structural proteins (NS1, NS2a, NS2b, NS3, NS4a, NS4b, NS5). Upon primary infection with DENV, antibodies against various dengue proteins are generated (Green and Rothman, *Current Opinion in Infectious Diseases* 19:429-436, 2006). Serotypes can be distinguished by using virus-specific antibodies or antigens.

Typically, immunity against the infective serotype ensues, but protection against other serotypes is only for a short period of time. During a second infection by a different serotype, the presence of neutralizing antibodies may reduce the severity of the disease. However, the repertoire of sub-neutralizing antibodies can form complexes with dengue viruses that can bind to the FcγR resulting in an augmentation of the virus infection. The augmentation of viral infection is called the antibody dependent enhancement (ADE) (Green and Rothman, *Current Opinion in Infectious Diseases* 19:429-436, 2006; Guzman and Kouri. *The Lancet Infectious Diseases* 2:33-42, 2002; Kliks et al., *Am J Trop Med Hyg* 40:444-51, 1989; Oishi et al., *J Med Virol* 71:259-64, 2003; Stephenson, *Bulletin of the World Health Organization* 83:308-14, 2005). Many epidemiological studies have found an increased risk of DHF after a second infection with a different serotype (Guzman et al., *Int. J Infect. Dis* 6:118-24, 2002; Graham et al. *Am J Trop Med Hyg* 61:412-19, 1999; Thomas et al., *Am J Trop Med Hyg* 78:990-8, 2008). During ADE it is believed that neutralizing antibodies generated during the adaptive immune response cross-react, but do not neutralize, a second infecting dengue virus serotype. These antibody-viral complexes are taken up by monocytes by binding the cell-surface Fc receptors, resulting in increased viral loading. As a result, highly activated monocytes release cytokines and factors involved in vascular leakage. Other evidence points to DHF being the result of an interplay between host and viral factors (Martina et al. *Clin. Microbiol. Rev.* 22:564-81, 2009).

Population-based studies have shown that the severity of the disease increases with the patient's age (Burke, *Am J Trop Med Hyg* 38:172-80, 1988; Cobra et al., *Am J Epidemiology* 142:1204-11, 1995; Dietz et al., *Puerto Rico Health Sciences Journal* 15:201-10, 1996; Kuberski et al., *Am J Trop Med Hyg* 26:775-83, 1977). DF is an acute febrile disease often characterized by frontal headache, retroocular pain, muscle and joint pain, nausea, vomiting, and rash (Kalayanarooj et al., *J Infect Dis* 176:313-21, 1997). The febrile period usually terminates between 5-7 days after the onset of symptoms, often correlating with the disappearance of the virus from the circulation. DHF is an acute febrile illness, typically with bleeding, thrombocytopenia, elevated hematocrit, pleural effusions, and hypoproteinaemia. It begins as DF with a sudden onset of fever, and then develops into DHF around 3-7 days of illness (around the time of defervescence for DF) and continues for about 2-7 days. The main pathophysiological difference between DF and DHF is plasma leakage. Dengue shock syndrome (DSS) is the most severe form of the disease characterized by circulatory failure and a narrowing pulse range. Once shock begins, the fatality rate can be as high as 44% if the proper precautions are not taken (Oishi et al., *J Med Virol* 71:259-64, 2003). Diagnosis and characterization of a dengue infection needs to be early in disease progression to maximize the patient's chance of survival.

Diagnosis of dengue virus infection can be made by physical examination of the patient and routine clinical laboratory tests such as complete blood count (CBC). A positive tourniquet test has been considered to be a sensitive parameter for dengue diagnosis. More than 90% of cases can be correctly diagnosed for dengue infection by history, physical signs, and a positive tourniquet test. However, definitive diagnosis for dengue virus as a causative agent requires laboratory confirmation, especially in regions where other endemic infectious diseases (viral and parasitic (e.g., malaria)) mimic the syndromes caused by dengue infection. Definitive diagnostic tests for dengue infection include isolation of viable virus and identification of viral RNA in serum or plasma. Several factors, such as timing of specimen collection and availability of equipment limit routine application of these tests.

Serological techniques are also used for dengue diagnosis. Because timing of specimen collection is flexible and immunoglobulins are not easily degraded or inactivated by harsh treatment of specimens, serological tests are commonly used in the field. The most commonly used serological techniques for the diagnosis of dengue infection are the hemagglutination inhibition (HI) test, which detects total anti-dengue antibodies by the ability of dengue antibody to inhibit dengue virus-mediated agglutination of erythrocytes from geese or trypsinized human O red blood cells, and the immunoglobulin M or G (IgM or IgG) capture enzyme linked immunosorbent assay (ELISA). HI test and IgG-captured ELISA usually require paired acute and convalescent phase serum samples collected a week or more apart for definitive diagnosis based on a fourfold rise in anti-dengue antibody. Results from both IgM and IgG capture ELISA can be used to differentiate between the cases of primary and secondary infection. In primary infection, the ratio of anti-dengue IgM to anti-dengue IgG is relatively high for at least a month following infection, but in secondary infection, a rapid increase of IgG antibody generally occurs following infection, and the ratio of anti-dengue IgM to anti-dengue IgG in a single acute specimen is low.

I. Biomarkers

Certain embodiments are directed to the use of biomarkers differentially present in subjects at risk of developing or having DHF or DSS. A biomarker is a biomolecule that is differentially present in a sample taken from a subject of one phenotypic status (e.g., DF) as compared with another phenotypic status (e.g., DHF). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

Certain embodiments are directed to methods for identifying subjects at risk for DHF based on one or more factors including clinical features, biochemical assays, and gene expression profiling. However, identification of predictive biomarkers in complex biofluids, such as plasma, have been challenging for proteomics technologies. Plasma is a complex biofluid, with its constituent proteins present in a broad dynamic concentration range spanning 12 log orders of magnitude or more (Anderson and Anderson *Mol Cell Proteomics* 1:845-67, 2002; Rifai and Gerszten, *Clinical Chemistry* 52:1635-37, 2006). Moreover, the tendency of high-abundance proteins to adsorb lower-abundance proteins and peptides (Gundry et al. *Proteomics Clin. Appl.* 1:73-88, 2007; Seferovic et al., *J Chrom. B Analyt. Technol. Biomed. Life Sci.* 865:147-152, 2008), the presence of proteases that may produce peptide fragments (Villanueva et al., *J Proteome Res.* 4:1060-72, 2005; Villanueva et al., *Mol. Cell Proteomics* 7:509-18, 2008), and the individual variation in plasma protein abundances serve to compound the difficulties in comprehensive proteomic analyses of plasma.

Recent advances in global scale proteomics technologies enable the detection of candidate protein biomarkers. These biomarkers include proteins, peptides, or metabolites whose measurement alone (or in a combination) would reliably indicate disease outcome. With the advancement of multi-dimensional profiling techniques, the systematic and quick identification of predictive proteins associated with a disease is now feasible.

In certain aspects, biomarkers for DHF include, but are not limited to complement Factor D, complement Factor H, high molecular weight albumin, desmoplakin, and IL2.

Complement factor D (Factor D) is encoded by the CFD gene. Factor D is involved in the alternative complement pathway of the complement system where it cleaves factor B. The protein encoded by this gene is a member of the trypsin family of peptidases. This protein is also a serine protease that is secreted by adipocytes into the bloodstream.

Complement factor H (Factor H) is a member of the regulators of complement activation family and is a complement control protein. It is a large (155 kilodaltons), soluble glycoprotein that circulates in human plasma (at a concentration of 500-800 micrograms per milliliter). Its principal function is to regulate the Alternative Pathway of the complement system, ensuring that the complement system is directed towards pathogens and does not damage host tissue. Factor H regulates complement activation on self cells by possessing both cofactor activity for the Factor I mediated C3b cleavage, and decay accelerating activity against the alternative pathway C3 convertase, C3bBb.

High molecular weight (hMW) albumin is one of the main proteins of plasma. High molecular weight albumin includes the cross-linked isoforms of albumin, e.g., those having a molecular weight of greater than 200 kDa, which includes both albumin*2 and albumin*3 (MW~263 kDa), but not albumin*1 (MW=52 kDa). Albumin binds water, cations (such as Ca2+, Na+ and K+), fatty acids, hormones, bilirubin, thyroxine (T4), and various drugs. Albumins main function is to regulate the colloidal osmotic pressure of blood.

Desmoplakin is a protein that in humans is encoded by the DSP gene. Desmosomes are intercellular junctions that tightly link adjacent cells. Desmoplakin is an obligate component of functional desmosomes that anchors intermediate filaments to desmosomal plaques. The N-terminus of desmoplakin is required for localization to the desmosome and interacts with the N-terminal region of plakophilin 1 and plakoglobin. The C-terminus of desmoplakin binds with intermediate filaments.

Interleukin-2 (IL-2) is an interleukin, a type of cytokine signaling molecule in the immune system. It is a protein that attracts white blood cells (lymphocytes of leukocyte), the cells that are responsible for immunity. It is part of the body's natural response to microbial infection, and in discriminating between foreign (non-self) and self. IL-2 mediates its effects by binding to IL-2 receptors, which are expressed by lymphocytes.

II. Assays for the Detection of Biomarkers

Any suitable method may be used to detect the biomarkers in a biological sample in order to determine the level(s) of the one or more biomarkers. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof (e.g. LC-MS-MS). Further, the level(s) of the one or more biomarkers may be detected indirectly, for example, by using an assay that measures the level of a compound (or compounds) that correlates with the level of the biomarker(s) that are desired to be measured.

In certain aspects, the biomarkers of this invention can be measured or detected by immunoassay or mass spectrometry. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

In certain aspects, a sample may be contacted with an antibody specific for a biomarker under conditions sufficient for an antibody-biomarker complex to form, and then detecting the complex. Detecting or measuring a biomarker may be accomplished in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279, and 4,018,653, each of which is incorporated herein by reference. These include both single-site and two-site or "sandwich" assays of the non-competitive types, as well as in the traditional competitive binding assays. These assays also include direct binding of a labeled antibody to a target biomarker.

In certain aspects the sandwich assay is used to detect or measure a biomarker. A number of variations of the sandwich assay technique exist, and all such techniques can be used in practice of the methods described herein. Briefly, in a typical forward assay, an unlabeled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated, e.g., by comparing with a control sample containing known amounts of biomarker or a standard.

Variations on the forward assay include a simultaneous assay, in which both sample and labeled antibody are added simultaneously to the bound antibody. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes generally consist of cross-linking, covalently binding, or physically adsorbing a capture agent (e.g., an antibody) to a surface, the surface-capture agent complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C., such as between 25° C. and 32° C., including all values and ranges there between) to allow binding of any subunit present in the antibody. Following the incubation period, the antibody subunit solid phase is washed and dried and incubated with a second antibody specific for a portion of the biomarker. The second antibody is linked to a reporter molecule that is used to indicate the binding of the second antibody to the biomarker.

An alternative method involves immobilizing the target biomarkers in the sample and then exposing the immobilized target to a specific antibody that may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule that, by its chemical nature, provides an analytically identifiable signal allowing detection of antigen-bound antibody. Reporter molecules include, but are not limited to enzymes, fluorophores, radionuclides, and chemiluminescent molecules.

In the case of an enzyme immunoassay, an enzyme is conjugated to the second antibody, generally by means of glutaraldehyde or periodate. A wide variety of different conjugation techniques exist, each of which may be used to produce a conjugate described herein. Commonly used enzymes include horseradish peroxidase, glucose oxidase, β-galactosidase, and alkaline phosphatase, amongst others. The substrates to be used with the specific enzymes are generally chosen for the production, upon hydrolysis by the corresponding enzyme, of a detectable signal. Examples of suitable enzymes include alkaline phosphatase and peroxidase. It is also possible to employ fluorogenic substrates, which yield a fluorescent product rather than the chromogenic substrates. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of detectable signal. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Other reporter molecules, such as radioisotope, chemiluminescent or bioluminescent molecules, may also be employed.

Biomarkers can be detected and measured using mass spectrometry (MS). MS is a technique for measuring and analyzing molecules that involves fragmenting a target molecule, then analyzing the fragments, based on their mass/charge ratios, to produce a mass spectrum that serves as a "molecular fingerprint". Determining the mass/charge ratio of an object is done through means of adjusting a magnetic field to direct ions of appropriate mass and charge into the detector region of the mass spectrometer and measuring the current necessary to replace electrons that have been depleted by the appearance of the ion at the detector surface. There are several commonly used methods to determine the mass to charge ratio of an ion, some measuring the interaction of the ion trajectory with electromagnetic waves, others measuring the time an ion takes to travel a given distance, or a combination of both. The data from these fragment mass measurements can be searched against databases to obtain definitive identifications of target molecules.

An embodiment of a method for identifying patients with risk of developing DHF, comprising one or more of the following steps:

(1) obtaining a plasma sample from a patient with presenting symptoms of Dengue disease;

(2) detecting the presence and/or amount of IL-10, tropomyosin, complement 4A, immunoglobulin V, fibrinogen, albumin*1, albumin*2 and albumin*3 in said sample; and (3) correlating a patient's risk of developing DHF to presences of IL-10, tropomyosin, complement 4A, immunoglobulin V, fibrinogen, albumin*1, albumin*2 and albumin*3 in said sample.

In various configurations, the methods comprise determining the presence, absence, or quantity of biomarkers in plasma of an individual presenting symptoms of Dengue disease including IL-10, tropomyosin, complement 4A, immunoglobulin V, fibrinogen, and three isoforms of albumin. In various aspects, an individual is considered to be at risk of developing DHF if these biomarkers are detected. Accordingly, medical intervention can be performed before symptoms of DHF progress.

In various configurations, determining presence, absence or quantity of one of these seven proteins can comprise (a) contacting a plasma sample from an individual with a solid surface comprising a first probe which specifically binds to one of the targeted biomarker, wherein a complex forms comprising the probe and the that biomarker, if present in the sample, (b) contacting the solid surface with a second probe which specifically binds that biomarker; and (c) determining quantity of the second probe bound to the surface.

In one embodiment, a health care provider such as a medical doctor can make a decision on whether to treat the individual, and which modalities of treatment to use, on the basis of the subject individual's profile of biomarkers including IL-10, tropomyosin, complement 4A, immunoglobulin V, fibrinogen, and three isoforms of albumin in plasma.

In another embodiment, types of probes that can be used in the present methods include, without limitation, antibodies, aptamers, kinases, avimers and combinations thereof. Antibodies can be monoclonal antibodies, polygonal antibodies or combinations thereof, and aptamers can be RNA aptamers, DNA aptamers, peptide aptamers, or combinations thereof.

A solid surface can be, without limitation, an ELISA plate, a bead, a dip stick, a test strip, or a microarray.

In various aspects, binding of a second probe to a solid surface can be detected using any type of label known to skilled artisans, such as, for example, a fluorophore such as fluorescein, rhodamine, Cy3 or an ALEXA dye of Molecular Probes™ (Invitrogen), a hapten such as biotin or digoxygenin, an enzyme such as horseradish peroxidase, alkaline phosphatase, chloramphenicol acetyltransferase or luciferase, or a radioisotope. In various configurations, a hapten label can be detected by a secondary probe well known to skilled artisans, such as, for example, an enzyme-conjugated antibody directed against biotin or digoxygenin, or an enzyme-conjugated avidin or streptavidin. In addition, binding of a second probe to a solid surface can be quantified using any methods and devices known to skilled artisans, such as, without limitation, measuring fluorescence of a fluorophore linked to a second probe using a fluorimeter, or measuring light absorbance of a chromophore generated by hydrolysis of a chromogenic substrate of an enzyme linked to a secondary probe.

In various embodiments, linkage of a label to a second probe can be direct (for example, an enzyme such as horseradish peroxidase covalently attached to an antibody directed against the target protein or indirect (for example, an enzyme covalently attached to goat anti-mouse serum, when the second probe is a mouse monoclonal antibody directed against the target protein, and when the first probe is not a mouse antibody).

In another embodiment, a kit comprises components to be used to assess individual risk of developing DHF. A kit of this embodiment comprises a set of first probes each specifically binds to one of the target biomarker; and a set of second probes which specifically binds that each of the target biomarker. In various aspects of a kit of these embodiments, the probes and labels can be of any of the types described above. In some aspects, each probe can be an antibody independently selected from the group consisting of a polyclonal antibody and a monoclonal antibody. In some aspects, a second probe comprised by a kit can further comprise a label. However, in some aspects, if a first antibody and a second antibody are directed against the same antigen and the antibodies derive from the same species, the second antibody has a label that allows it to be detected and quantified independent of detection of the first antibody.

III. Diagnostic Kits for Early Detection of Dengue Hemorrhagic Fever

In another aspect, the present invention provides kits for qualifying Dengue disease status, which kits are used to detect biomarkers described herein. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

IV. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Factors and DHF Detection Modeling Study I

To identify differentially expressed proteins associated with DHF, a reproducible, novel pre-separation fractionation method is developed, and is termed the biofluid analysis platform (BAP). BAP takes advantage of high recovery and quantitative size exclusion fractionation, followed by quantitative saturation fluorescence labeling, two dimensional gel electrophoresis (2-DE), and LC-MS/MS (liquid chromatography-tandem mass spectrometry) to identify differentially expressed proteins associated with DHF. Plasma samples from 53 volunteers (42 DF and 13 DHF) with initial clinical presentation of Dengue infection were obtained and subjected to focused and discovery-based proteomic using ELISA and BAP.

Demographics, clinical laboratory measurements, 9 cytokines and 419 plasma proteins at the time of initial presentation were compared between the outcomes of Dengue Fever and Dengue Hemorrhagic Fever. Statistical comparison showed that the subject's gender, clinical parameters, 2 cytokines, and 42 proteins discriminated between the groups, but importantly, gender contributed significant interactions. Because statistical analysis of discriminant proteins indicates that the proteins are not normally distributed, conventional parametric modeling approaches are precluded. These factors were reduced by a nonparametric classification approach, multivariate adaptive regression splines (MARS), where a highly accurate classifier of the sample set including IL-10 and 7 plasma proteins was obtained using cross-validation.

Figure 1B:
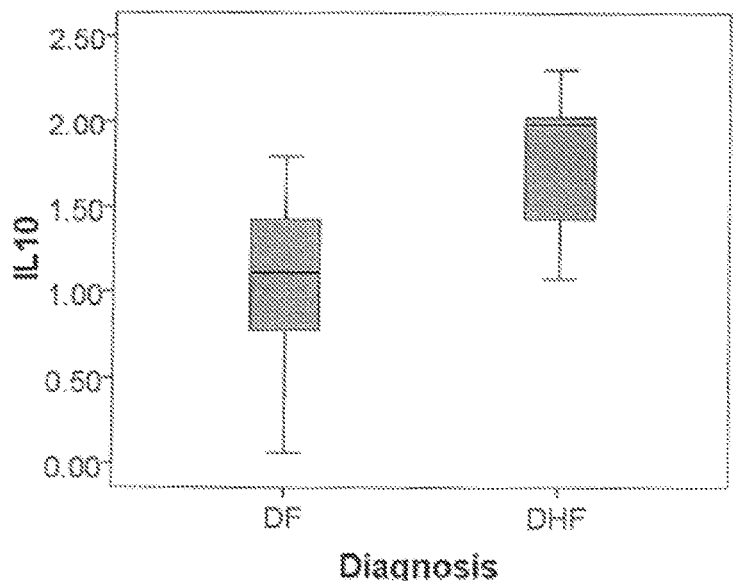

Cytokine analyses. Focused proteomics analyses were performed using bead-based immunoplex to measure cytokines that have been associated with DHF in previous studies (Bozza et al., *BMC Infectious Diseases* 8:86, 2008; Perez et al., *J Med Virol* 73:230-34, 2004); these measurements included IL-6, IL-10, IFN-α, IP-10, MIP-1α, TNFα, IL-2, CD309 (VEGF), and CD262 (TRAIL). Analysis of the plasma concentrations of the cytokines indicated that their distributions were highly skewed; despite logarithmic transformation of the data, the data remained non-normally distributed. As a result, the cytokines were compared between the two outcomes using the Wilcoxon rank-sum test. A permutation test was used to derive p-values based on the violation of normal assumption. Only two cytokines retained significance between DF and DHF, IL-6 ($p=0.002$) and IL-10 ($p<0.001$) (FIGS. 1A and 1B). For both cytokines, the median value of the log 2-transformed concentration was greater in DHF than that of DF subjects.

Differences between cytokines were analyzed as a function of gender using two-factor ANOVA. For IL-6 and IL-10, MIP-1α, and TRAIL, gender is found significant for diagnosis (DF vs DHF) effect (Table 1). To correct for correlated cytokines, a MANOVA test was applied to the overall data. In this analysis, both gender (p=0.0165) and diagnosis (p<0.0001) had significant Wilks-Lamba p values. Together, these analyses indicate that gender is an important confounding variable in the cytokine response to dengue infection.

TABLE 1

Two-way ANOVA for detection of interactions between gender and disease. Df, degrees of freedom; Sig., significance.

| Cytokine | Source | Type III Sum of Squares | Df | Mean Square | F | Sig. |
|---|---|---|---|---|---|---|
| IL-6 | Disease | 0.637 | 1 | 0.637 | 11.034 | 0.002 |
|  | Gender | 0.335 | 1 | 0.335 | 5.795 | 0.020 |
|  | Disease* Gender | 0.032 | 1 | 0.032 | 0.559 | 0.459 |
|  | Error | 2.715 | 47 | 0.058 |  |  |
|  | Total | 3.557 | 50 |  |  |  |
| IL-10 | Disease | 4.643 | 1 | 4.643 | 28.675 | 0.000 |
|  | Gender | 0.667 | 1 | 0.667 | 4.182 | 0.046 |
|  | Disease*Gender | 0.231 | 1 | 0.231 | 1.428 | 0.238 |
|  | Error | 7.610 | 47 | 0.162 |  |  |
|  | Total | 12.531 | 50 |  |  |  |

Biofluid analysis platform (BAP). To more comprehensively identify proteins associated with the development of DHF, a discovery-based sample pre-fractionation method was applied with 2DE using saturation fluorescence labeling, together termed a biofluid analysis platform (BAP). The BAP combines a high recovery Superdex S-75 size-exclusion chromatography (SEC) of plasma with electronically triggered fraction collection to create protein and peptide pools for subsequent separation and analysis. An important feature of the BAP is the utilization of de-ionized urea to initially dissociate protein/peptide complexes in the plasma prior to SEC.

The initial denaturation of the plasma prior to rapid SEC fractionation avoids the pitfall of peptide binding to high abundance plasma carrier proteins (Gundry et al., Proteomics Clin. Appl. 1:73-88, 2007; Seferovic et al., J Chromatogr. B Analyt. Technol. Biomed. Life Sci. 865:147-52, 2008). Moreover, SEC is a non-adsorptive, high recovery pre-fractionation approach that achieves 95-100% recovery of the input protein. Downstream of SEC, antibody depletion results in significant increase in proteome coverage, enhancing detection of low abundance proteins (Tu et al., J. Proteome Res. 9:4982-91, 2010). Finally, our development of a quantitative saturation fluorescence labeling produces 2DE to identify differentially expressed proteins (Pretzer and Wiktorowicz, Anal. Biochem. 374:250-262, 2008).

One hundred and six serum samples, representing acute and convalescent samples from 53 subjects were analyzed by BAP. Four hundred and nineteen spots were mapped and the normalized spot intensities were compared. For the purposes of biomarker panel development, normalized spot intensities were compared between DF and DHF in the acute samples. From this analysis, 34 spots met statistical cut-off criteria (p<0.05, t-test).

Multivariate Adaptive Regression Spline (MARS)-based Modeling for Predictors of DHF. Because the proteomic quantifications violated normal distributions and included outliers, nonparametric modeling methods were used. MARS is a robust, nonparametric, piecewise linear approach that establishes relationships within small intervals of independent variables, detects feature interactions and is generally resistant to the effects of outlier influence (Cook et al., Statistics in Medicine 23:1439-1453, 2005). MARS can estimate complex nonlinear relationships by a series of spline functions of the predictor variables. Regression splines seek to find thresholds and breaks in relationships between variables and are very well suited for identifying changes in the behavior of individuals or processes over time. Some of the advantages of MARS are that it can model predictor variable of many forms, whether continuous or categorical, and can tolerate large numbers of input predictor variables and can easily deal with missing values. As a nonparametric approach, MARS does not make any underlying assumptions about the distribution of the predictor variables of interest.

Figure 2:
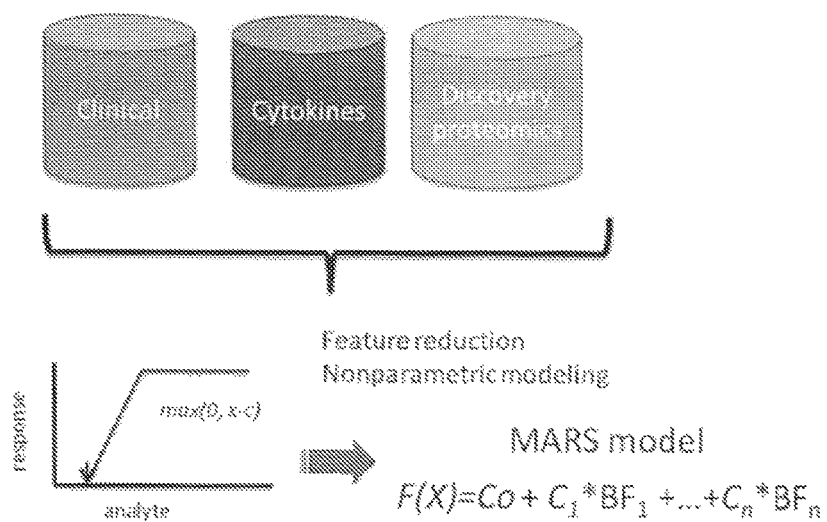
FIG. 2. MARS modeling strategy. Shown is a schematic diagram of modeling strategy to identify predictors of DHF using different data types. Data sources include: clinical demographics, normalized spot intensities by 2DE analysis and log 2-transformed cytokine measurements. MARS produces a linear combination of basis functions (BFs), each represented by the value of the maximum of (0, x-c), where x is the analyte concentration.
Figure 3:
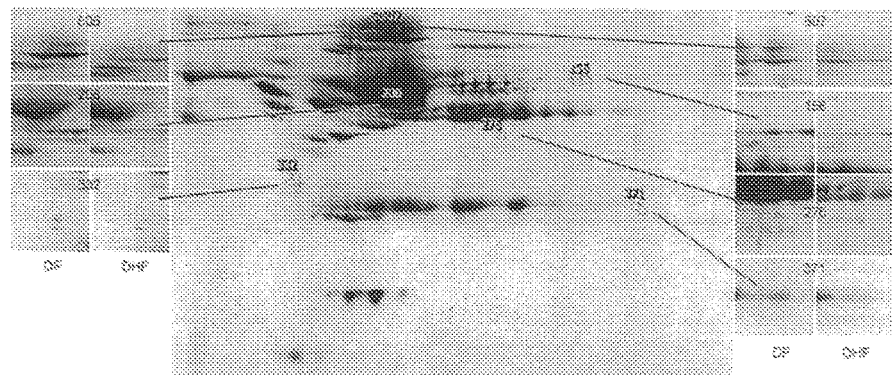
FIG. 3. 2DE images. Shown is a reference gel of 2DE of BAP fractionated and IgY depleted plasma from the study subjects. The location of protein spots that contribute to the prediction of DHF are indicated. Insets, spot appearances for reference gels for DHF and DF. Spot 156 (C4A), 206 (albumin*1), 276 (fibrinogen), 332 (tropomyosin), 371 (immunoglobulin gamma-variable region), 506 (albumin*2) and 507 (albumin*3).

To identify features important in DHF, gender, logarithm-transformed cytokine expression values (IL-6 and IL-10), and 34 2DE protein spots were modeled using 10-fold cross-validation and a maximum of 126 basis functions, schematically diagrammed in FIG. 2. The optimal model was selected on the basis of the lowest cross-validation error, which included 1 cytokine (IL-10) and 7 protein spots including: tropomyosin, complement 4A, immunoglobulin V, fibrinogen, and three isoforms of albumin. The proteins that corresponded to each predictive spot were identified by LC-MS/MS analysis (Table 2). The confidence for identification of each protein was high, given as the expectation score. The location of the 7 proteins spots on 2DE and the effect of disease on their abundance is shown in FIG. 3. The 2DE analysis provided additional information not accessible by shotgun-based mass spectrometry. For example, the albumin isoforms were distinct isoforms of albumin as indicated by their unique isoelectric points (Table 2, FIG. 3). Moreover, two of the albumin isoforms, represented as spots 505 and 507, were much larger than native albumin, suggesting that they were cross-linked proteins.

TABLE 2

Protein Identification of MARS features. Shown are the protein identifications for the 2DE proteins identified that contribute to the MARS predictive classifier for DHF.

| No. | Protein name | GI Accession No. | UniProt Accession No. | Gel Spot No. | pi | MW (Da) | MSID Expectation Value |
|---|---|---|---|---|---|---|---|
| 1 | C4A | 239740686 | XP_002343974 | 156 | 8.18 | 71 | 5.00E−10 |
| 2 | Albumin * | 168988718 | P02768 | 206 | 6.28 | 52 | 2.51E−57 |
| 3 | Fibrinogen | 237823914 | P02671 | 276 | 7.35 | 40 | 9.98E−38 |

TABLE 2-continued

Protein Identification of MARS features. Shown are the protein identifications for the 2DE proteins identified that contribute to the MARS predictive classifier for DHF.

| No. | Protein name | GI Accession No. | UniProt Accession No. | Gel Spot No. | pi | MW (Da) | MSID Expectation Value |
|---|---|---|---|---|---|---|---|
| 4 | Tropomyosin | 10441386 | AAG17014 | 332 | 5.08 | 29 | 1.58E−41 |
| 5 | Immunoglobulin gamma V | 567146 | AAA52924 | 371 | 8.81 | 24 | 7.92E−04 |
| 6 | Albumin* | 168988718 | P02768 | 506 | 6.19 | 263 | 5.00E−47 |
| 7 | Albumin* | 168988718 | P02768 | 507 | 6.23 | 263 | 6.29E−32 |

A comparison of the normalized spot intensities for the 7 discriminant proteins were plotted by the outcome of Dengue disease (FIG. 6). Similar to the cytokine analysis, although the proteins differ by median value, the analysis of the distribution of normalized and logarithm-transformed protein concentrations, derived either from quantitative bead-based ELISA or normalized spot intensities from the saturation fluorescence labeled 2DE analysis, were highly overlapping (FIGS. 1 and 6), suggesting that, if used as single measurements, they would not be informative or robust biomarkers. Any singular protein would have poor ability to discriminate between disease types. Moreover, the protein concentrations were not normally distributed and therefore demand analysis by nonparametric methods.

The optimal MARS model is represented by a linear combination of 9 basis functions, where each basis function is a range over which the individual protein's concentration contributes to the classification basis functions, whose values are shown in Table 3 (A). Also of note, the basis functions are composed of single features, indicating that interactions between the features do not contribute significantly to the discrimination. Using combined BAP nonparametric MARS modeling approach, our most accurate model for the prediction of DHF was based on IL-1 0, C4A, fibrinogen, tropomyosin, immunoglobulin, and several albumin isoforms. This model was able to accurately predict DHF in 100% of the cases, and evaluation of the sensitivity-specificity relationship by ROC analysis indicated a very good fit of the model to our data. The model diagnostics using GAM further provide support that nonlinear approaches were appropriate to associate disease state with protein expression patterns. Prediction success is shown in Table 3 (B)

TABLE 3 (A)

MARS Basis Functions.

| $B_m$ | Definition | $a_m$ | Variable descriptor |
|---|---|---|---|
| BF1 | (IL-10-1.15)* | 5.83E−03 | IL-10 |
| BF3 | (20873 − Fibrinogen)* | 5.42E−05 | Fibrinogen |
| BF5 | (437613 − Albumin)* | 1.39E−06 | Albumin*1 |
| BF6 | (C4A − 385932)* | −4.90E−06 | Complement 4A |
| BF8 | (C4A − 256959)* | 3.25E−06 | Complement 4A |
| BF11 | (469259 − Albumin)* | 2.48E−06 | Albumin*2 |
| BF17 | (122218- TPM4)* | 5.27E−06 | TPM4 |
| BF19 | (Immunoglobulin gamma-57130)* | −1.35E−06 | Immunoglobulin gamma-chain, V region |
| BF23 | (657432 − Albumin)* | −9.97E−07 | Albumin*3 |

Shown are the basis functions (BF) for the MARS model for dengue hemorrhagic fever. Bm, each individual basis function, $a_m$, coefficient of the basis function.
(y)*= max(0, y).
*Variable isoforms likely due to post-translational modification and/or proteolysis.

TABLE 3 (B)

Confusion matrix for MARS classifier of DHF. For each disease (class), the prediction success of the MARS classifier is shown.

| | | Prediction | |
|---|---|---|---|
| Class | Total | DF (n = 38) | DHF (n = 13) |
| DF | 38 | 38 | 0 |
| DHF | 13 | 0 | 13 |
| Total | 51 | correct = 100% | correct = 100% |

To determine which of these features contribute the most information to the model, variable importance was assessed. Variable importance is a relative indicator (from 0-100%) for the contribution of each variable to the overall performance of the model (FIG. 3). The variable importance computed for the top three proteins was IL-10 (100%), with Albumin* 1 (50%) followed by fibrinogen (40%).

Example 2

Mars Model Diagnostics Validation of Study I

Figure 4:
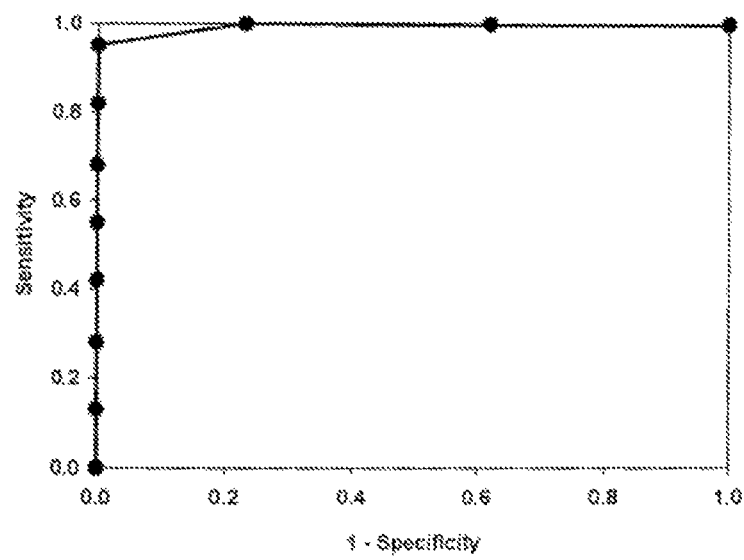
FIG. 4. ROC analysis. Shown is a Receiver Operating Characteristic (ROC) curve for the predictive model for DHF. Y axis, Sensitivity; X axis, 1-Specificity.
Figure 5:
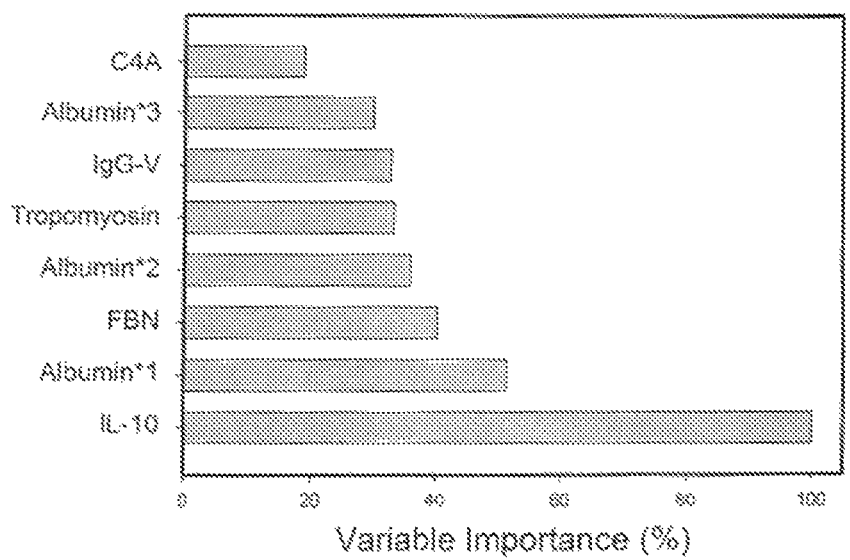
FIG. 5. Variable Importance for MARS model of DHF. Variable importance was computed for each feature in the MARS model. Y axis, percent contribution for each analyte.
Figure 6A:
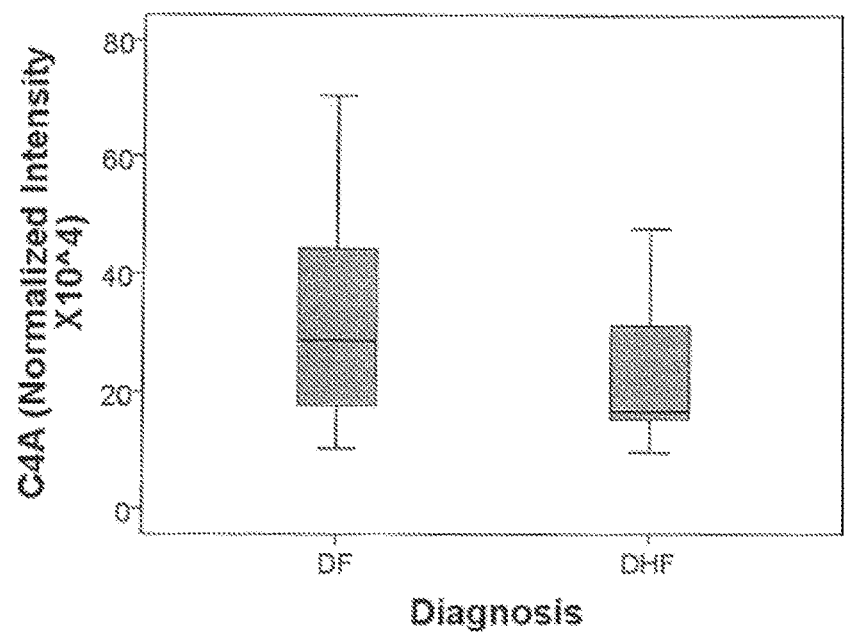
FIGS. 6A-6G. Differential 2DE spot expression in dengue fever. Shown is a boxplot comparison of 2DE spot expression values for C4A (FIG. 6A), Albumin*3 (FIG. 6B), IgG-V (FIG. 6C), Tropomyosin (FIG. 6D), Albumin*2 (FIG. 6E), fibrinogen (FBN, FIG. 6F), and Albumin*1 (FIG. 6G) by diagnosis. DF, Dengue fever; DHF, Dengue hemorrhagic fever. Horizontal bar, median value; shaded box, 25-75% interquartile range (IQR); error bars, median±1.5(IQR); *, outlier.
Figure 6B:
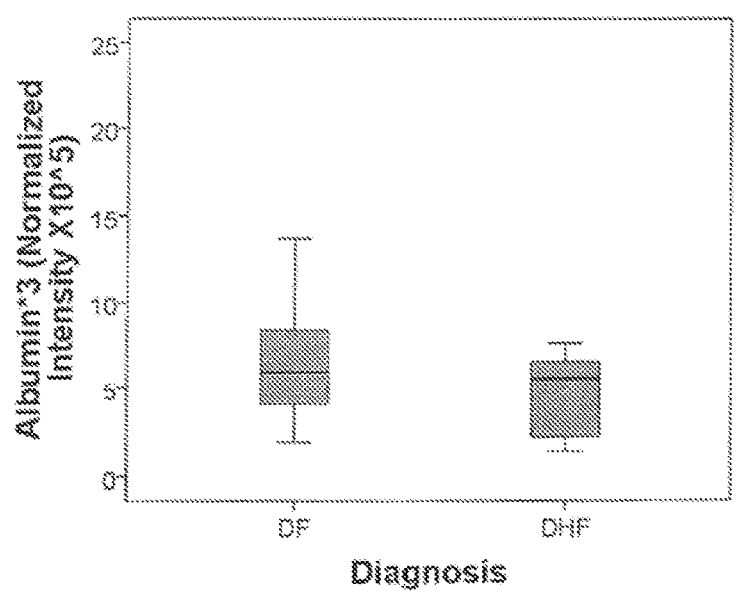
Figure 6C:
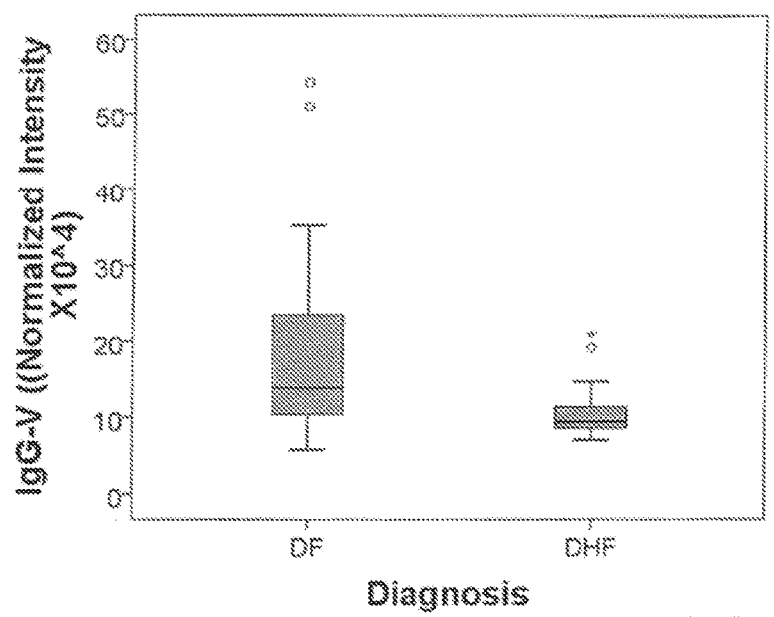
Figure 6D:
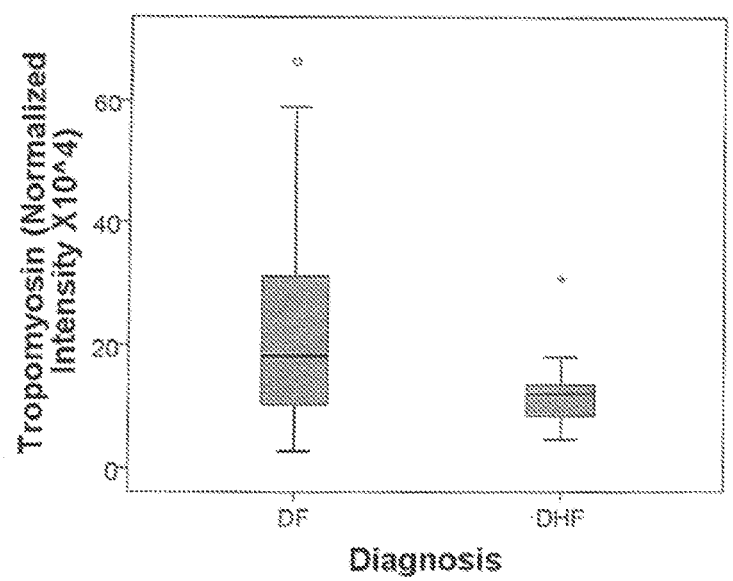
Figure 6E:
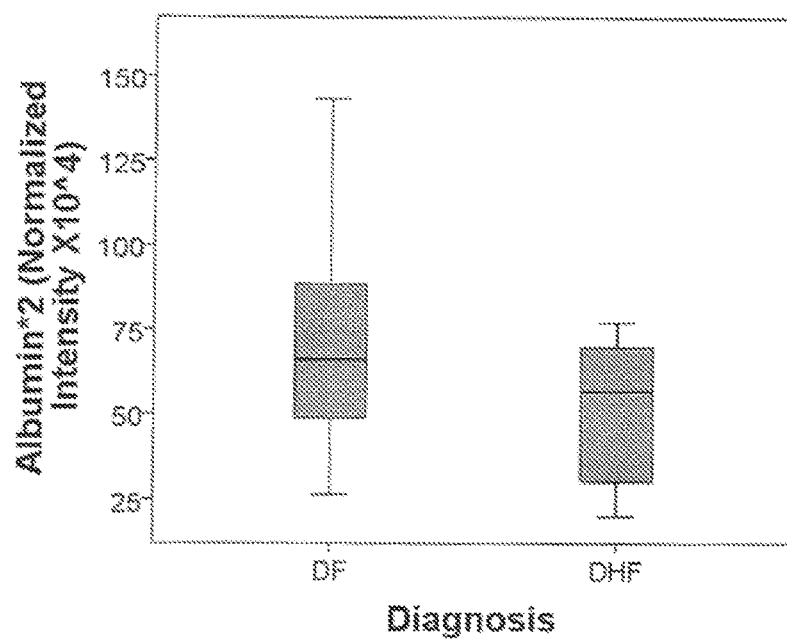
Figure 6F:
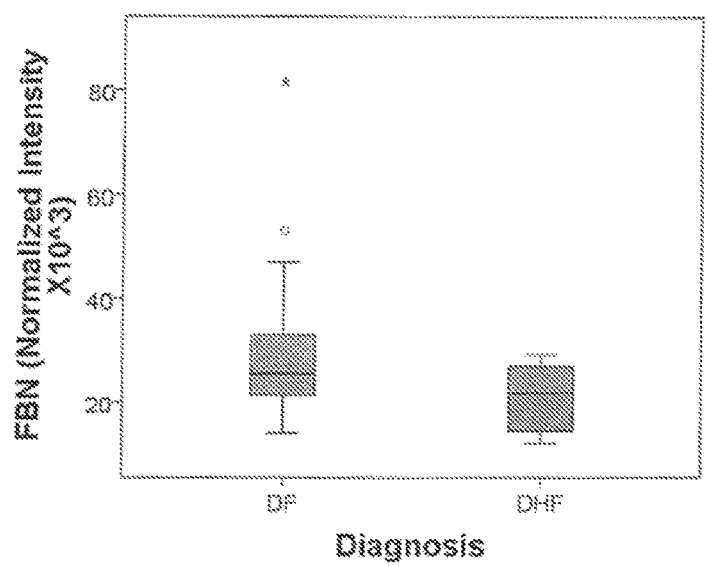
Figure 6G:
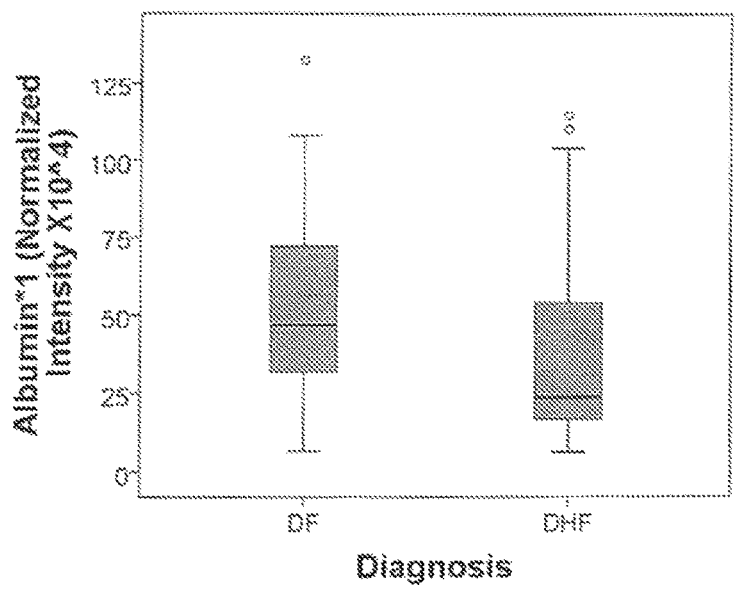
Figure 7A:
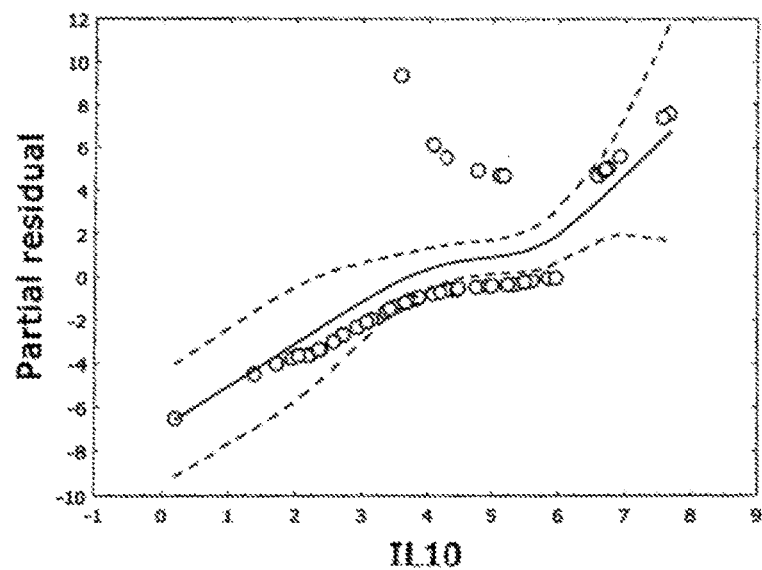
FIG. 7. Generalized Additive Model analysis. Shown are the partial residual plots for log-transformed values of 8 proteins important in MARS classifier. Y axis, partial residuals; X axis, log of respective feature. Note that regional deviations from classical linear model assumptions are seen.
Figure 7B:
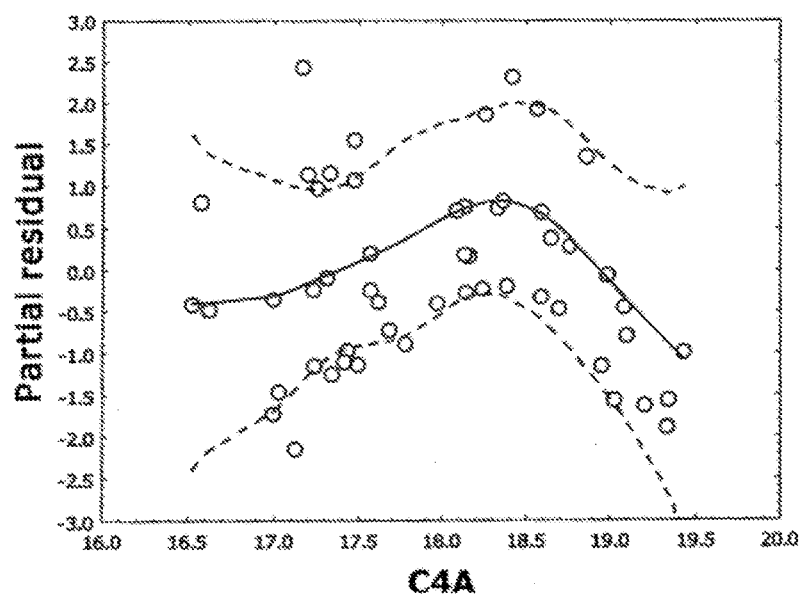
Figure 7C:
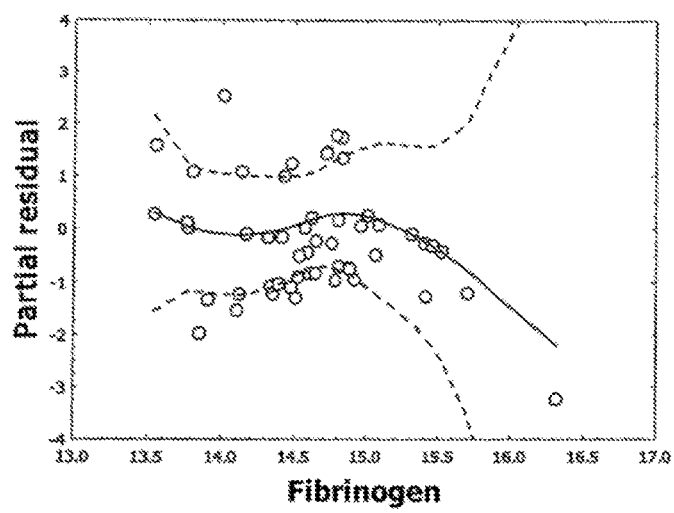
Figure 7D:
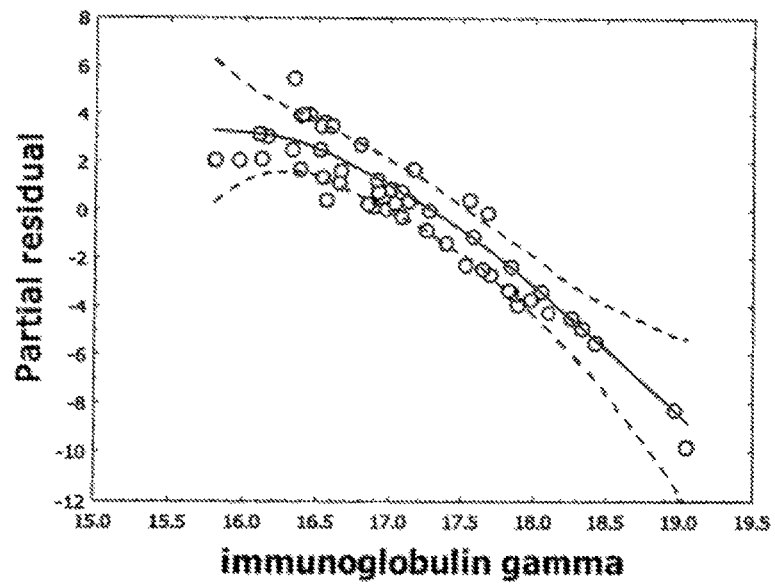
Figure 7E:
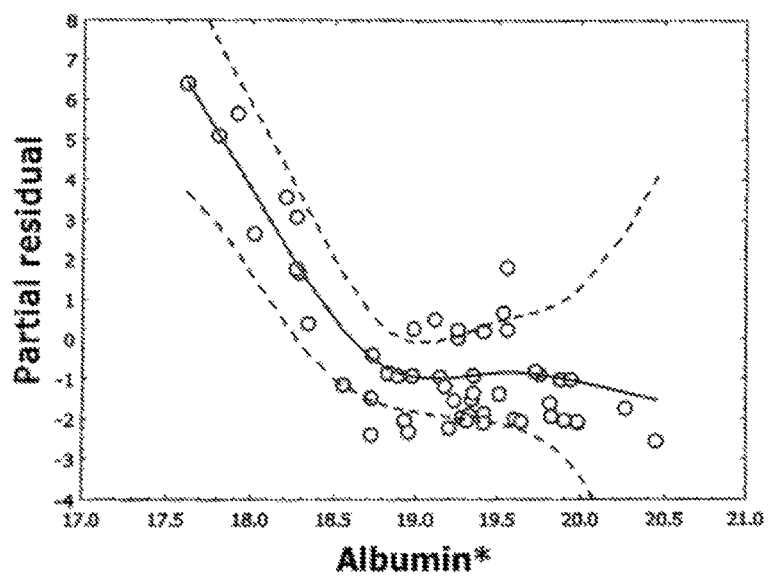
Figure 7F:
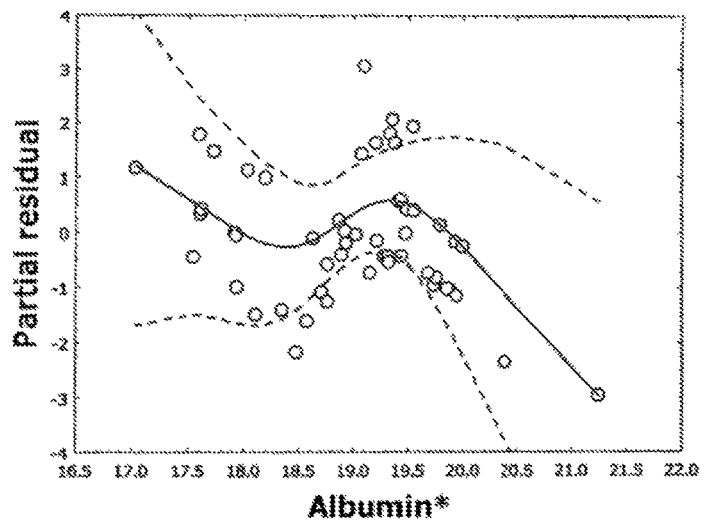

The performance of the MARS predictor of DHF was assessed using several approaches. First, the overall accuracy of the model on the data set was analyzed by minimizing classification error using cross-validation. The model accuracy produced 100% accuracy for both DHF and DF classification (Table 3). Another evaluation of the model performance is seen by analysis of the area under the Receiver Operating Characteristic (ROC) curve (AUC), where Sensitivity vs. 1-Specificity was plotted. In the ROC analysis, a diagonal line starting at zero indicated that the output was a random guess, whereas an ideal classifier with a high true positive rate and low false positive rate will curve positively and strongly towards the upper left quadrant of the plot (Fawcett. Pattern Recognition Letters 27:861-874, 2006). The AUC is equivalent to the probability that two cases, one chosen at random from each group, are correctly ordered by the classifier (Hanley and McNeil, Radiology 143:29-36, 1982). In the DHF MARS model, an AUC of 1.000 is seen (FIG. 4), indicating a highly accurate classifier on the data set.

Post-hoc generalized additive model (GAM) analysis. To confirm that a nonparametric method was the most appropriate modeling approach for these discriminant proteins, the predictive variables were subjected to a GAM analysis. GAMs are data-driven modeling approaches used to identify nonlinear relationships between predictive features and clinical outcome when there are a large number of independent variables (Austin, Stat. Med 26:2937-57, 2007; Hastie and Tibshirani, Stat. Methods Med Res 4:187-196, 1995).

Inspection of the residual plots for tropomyosin, complement 4, and albumin isoforms *1-*4 indicate that these variables do not satisfy classical assumptions for the use of linear modeling (FIG. 6). By contrast, IL-10 and immunoglobulin gamma approximate a global linear relationship. This analysis indicates that modeling approaches that assume global linear relationships, such as logistic regression, are not generally suited to relate information in proteomics measurements to clinical phenotypes or outcomes.

Previous work has shown that soluble mediators, including IL-2, IL-4, IL-6, IL-10, IL-13 and IFN-γ are found in plasma in increased concentrations in patients with severe dengue infections (Bozza et al., *BMC Infectious Diseases* 8:86, 2008). In a prospective study of a single serotype outbreak in Cuba, IL-10 was observed to be higher in individuals with secondary dengue infections (Perez et al., *J Med Virol* 73:230-234, 2004). It is also noted that dengue loading into monocytes in vitro resulted in enhanced IL-6 and IL-10 production (Chareonsirisuthigul et al., *J. Gen. Virol.* 88:365-75, 2007). The identification of IL-10 in this study as increased in DHF is a partial validation of our modeling.

Previous work has shown that immunological responses to vaccines are significantly affected by gender (Klein et al., *Lancet Infect. Dis.* 10:338-349, 2010). Interestingly, the two-factor ANOVA disclosed previously is the first observation to our knowledge that links gender to cytokine response in acute dengue fever infections. This gender effect confounds the statistical analysis of mixed gender population studies. Recognition of this finding will be important to guide the design of subsequent biomarker verification studies.

In the analysis of clinical parameters measured upon initial entry into the study showed that the platelet concentration is significantly reduced in subjects with DHF vs DF. Thrombocytopenia is a well established feature of DHF, responsible in part for increased tendency for cutaneous hemorrhages. The origin of thrombocytopenia in DHF is thought to be the consequence of both bone marrow depression and accelerated antibody-mediated platelet sequestration by the liver (Mitrakul et al., *Am J Trop Med Hyg* 26:975-84, 1977). Despite its statistical association with DHF, platelet counts do not contribute as strongly to an overall classifier of DHF as do circulating IL-10, immunoglobulin, and albumin isoforms. In addition to the tropism of dengue virus for monocytes and dendritic cells, severe dengue infections also involve viral-induced liver damage (Seneviratne et al., *Trans. R. Soc. Trop Med Hyg* 100:608-14, 2006). In this regard, increases in liver transaminases (LDH, AST) as well as decreases in albumin concentration have been observed (Villar-Centeno et al., *Am J Trop Med Hyg* 78:370-374, 2008). These phenomena probably represent leakage of hepatocyte cytoplasm and impairment in hepatic synthetic capacity, respectively. In this study, 2DE fractionation of plasma proteins provided an additional dimension of information not accessible by clinical assays. For example, the alternative migration of albumin isoforms (albumin *1-*3, FIG. 2), differing in molecular weight and isoelectric points, would not be detectable by mass spectrometry or by clinical assays. Although albumin is a target for nonenzymatic glycosylation and ischemia-induced oxidation, the biochemical processes underlying these changes in albumin in dengue infections are presently unknown.

Fibrinogen is an important predictor in the MARS model, with reduced and its concentration as a result of DHF (FIG. 6). Fibrinogen is a major component of the classical coagulation cascade. In this regard, coagulation defects, similar to mild disseminated intravascular coagulation, are seen in DHF. In fact, isotopic studies indicated a rapid turnover of fibrinogen (Srichaikul et al., *Am J Trop Med Hyg* 26:525-32, 1977), thereby explaining its reduction in patients with DHF measured by our analysis. Previous work using a 2D differential fluorescence gel approach comparing individuals with dengue fever versus normal controls, identified reduced fibrinogen expression (Albuquerque et al., *J. Proteome Res.* 8:5431-5441, 2009). However, from the design of this study, the use of fibrinogen to differentiate DF from DHF could not be assessed.

In summary, using nonparametric methods for developing predictive classifiers using a high resolution focused and discovery-based approach, a highly accurate classifier of DHF based on IL-1 0, fibrinogen, C4A, immunoglobulin, tropomyosin, and three isoforms of albumin were found. Most of these proteins can be linked to the biological processes underlying that of DHF, including cytokine storm, capillary leakage, hepatic injury, and antibody consumption, suggesting that these predictors may have biological relevance. All references cited in this application are herein incorporated by reference.

Example 3

Use of Factor D/Factor H, Desmoplakin, IL2 and High Molecular Weight Albumin as DHF Biomarkers-Study II Clinical human cohorts. The initial phase utilizes 45 representative plasma samples of dengue disease collected retrospectively from a well-characterized human clinical cohort in Recife, Brazil. In the state of Pernambuco where the city of Recife is the capital, DENY-1-3 have been circulating since 2002 and from 2004 to 2006, approximately 36,000 cases were reported. During this period, in Recife alone, 1,690 dengue fever cases and 29 DHF cases were confirmed. Forty-five of these samples serve as the basis to identify a limited set of predictive biomarkers for progression to severe disease. WHO Guidelines were used to classify dengue cases.

The inventors analyzed this dataset two separate ways. The first was to look at just the complement factors and see what type of model could be created using the current methods. The second was to create a model including the complement factors as well as the results from Bioplex cytokine assays and 2D gel electrophoresis.

Modeling DHF Using Complement Factors. This study included information about 11 complement factors: Factor D, Factor H, FD/FH, C5a, C3a, C4a, C1q, C3, MBL, CIC-C1q, and sC5b-9. For modeling purposes, the data needed to be complete (i.e., no missing values for various patients). Because of this restriction, only Factor D, Factor H, FD/FH, C1q, and C3 were used.

Multivariate Adaptive Regression Splines (MARS) is a nonparametric, multivariate regression method that can estimate complex nonlinear relationships by a series of spline functions of the predictor variables. Regression splines seek to find thresholds and breaks in relationships between variables and are very well suited for identifying changes in the behavior of individuals or processes over time. As a nonparametric approach, MARS does not make any underlying assumptions about the distribution of the predictor variables of interest. This characteristic is extremely important in our DHF modeling because many of the cytokine and protein expression values are not normally distributed, as would be required for the application of classical modeling techniques such as logistic regression. The basic concept behind spline models is to model using potentially discrete linear or nonlinear functions of any analyte over differing intervals. The resulting piecewise curve, referred to as a spline, is represented by basis functions within the model. To reduce overfitting models were restricted to those that incorporated one or fewer interaction terms.

Log based 2-transformed complement factor and gender were used to model DHF using MARS model specified 15 possible basis function and allowed only 1 interaction term. Ten-fold generalized cross-validation was used to avoid over-fitting the classification model (Salford Systems, Inc).

Unfortunately, the MARS model was unable to produce a highly accurate classifier of DHF. The resultant model was able to accurately predict DF status with 100% accuracy, but only 27% accuracy for the DHF patients. This resulted in an overall accuracy of 69%. The AUC (area under the curve) for such a model is 0.92.

Variable importance is a relative indicator (from 0-100%) for the contribution of each variable to the overall performance of the model. The only variable that was utilized in this model was FD/FH, which results in it having a variable importance of 100% in this particular context.

The optimal MARS model is represented by 1 basis function, whose equation is BF1=max(0, FD/FH−1.27677). Importantly this basis function is composed of a single feature, FD/FH, indicating that interactions between the complement measures do not contribute significantly to the discrimination. The resultant classification model for these 5 complement factors is Y=0.160568+0.424181*BF1.

DHF modeling Complement Factors, Cytokines, and Proteins. The inventors ran Bioplex cytokine assays for 11 cytokines Significant differences between DF and DHF within each of the cytokines were noted. Since Bioplex cytokine assay data is not normally distributed nonparametric tests were used to confirm, namely the Mann-Whitney test. The results of those tests are below in Table 4. Significant p-values (<0.05) are highlighted in yellow. This analysis was performed in SPSS v18.

TABLE 4

|  | Mann-Whitney U | Wilcoxon W | Z | Asymp. Sig. (2-tailed) |
|---|---|---|---|---|
| IL-2 | 205.000 | 458.000 | −2.316 | .021 |
| IL-6 | 150.000 | 403.000 | −3.334 | .001 |
| IL-10 | 243.000 | 708.000 | −1.611 | .107 |
| IFN-g | 222.000 | 475.000 | −2.001 | .045 |
| IP-10 | 222.000 | 687.000 | −2.000 | .045 |
| MIP-1a | 129.500 | 382.500 | −3.714 | .000 |
| TNF-a | 220.000 | 473.000 | −2.038 | .042 |
| VEGF | 129.000 | 382.000 | −3.723 | .000 |
| TRAIL | 278.000 | 531.000 | −.963 | .335 |
| IFN lambda1 (IL-29) | 316.500 | 781.500 | −.251 | .802 |
| IFN lambda2 (IL-28) | 267.500 | 732.500 | −1.288 | .198 |

The inventors also ran all samples on 2D electrophoresis gels. One thousand three hundred eleven (1311) protein spots were identified. Student's t-tests were run on the log 2 transformed intensities for each of the 1311 spots to detect significant differences between the DF and DHF patients. Of these 1311 spots, 121 had significant p-values (<0.05).

Figure 8:
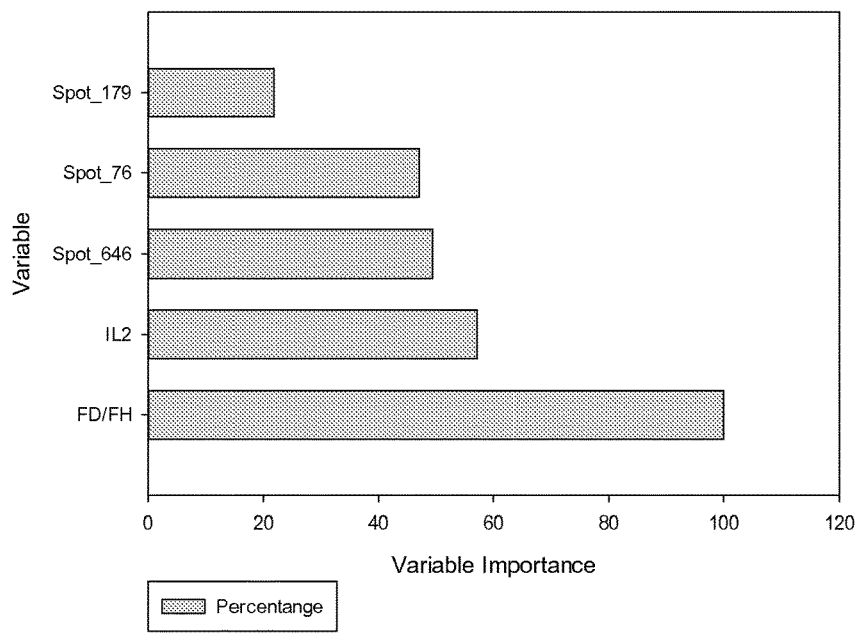
FIG. 8. Variable Importance for MARS model of DHF. Variable importance was computed for each feature in the MARS model. Y axis, percent contribution for each analyte.
Figure 9:
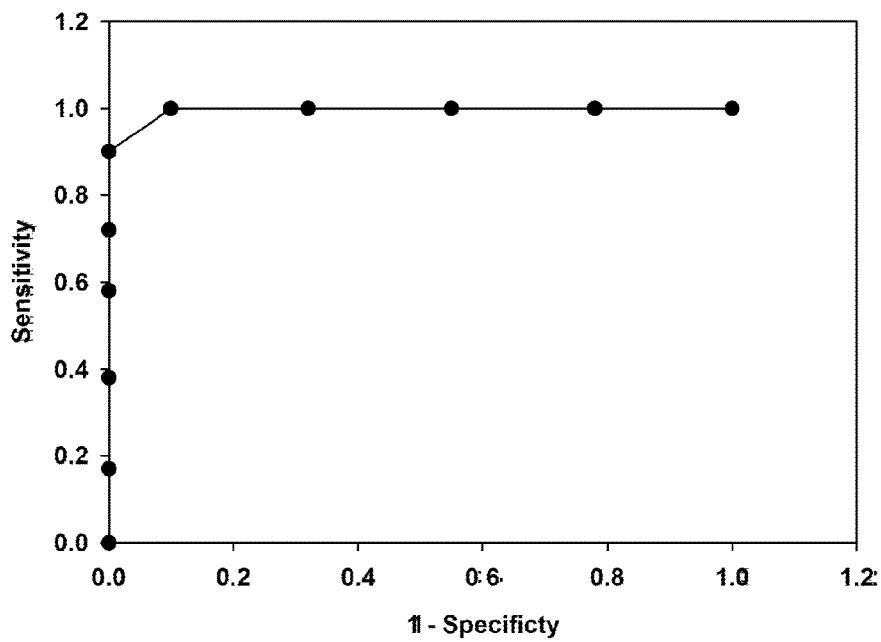
FIG. 9. ROC analysis. Shown is a Receiver Operating Characteristic (ROC) curve for the predictive model for DHF. Y axis, Sensitivity; X axis, 1-Specificity.
Figure 10:
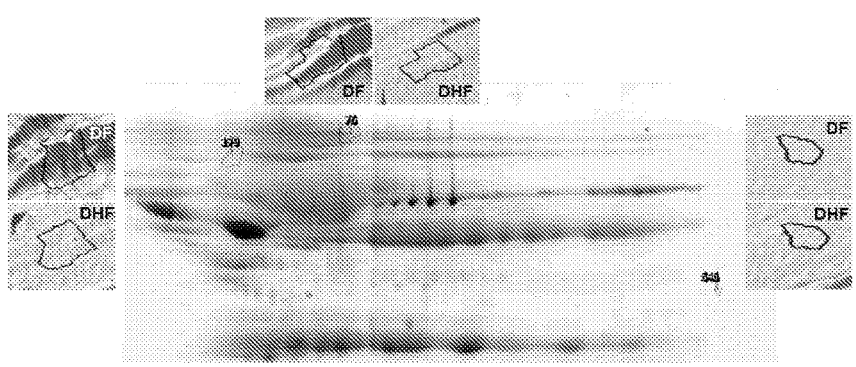
FIG. 10. Shows a reference gel of 2DE of BAP fractionated and IgY depleted plasma from the study subjects. The protein spots that contribute to the prediction of DHF are indicated. Insets, spot appearances for reference gels for DHF and DF. The location of spots 179, 76 and 646, identified as discriminant proteins in the MARS model are shown. Insets are the 3D view of the spot for DF and DHF.
Figure 11:
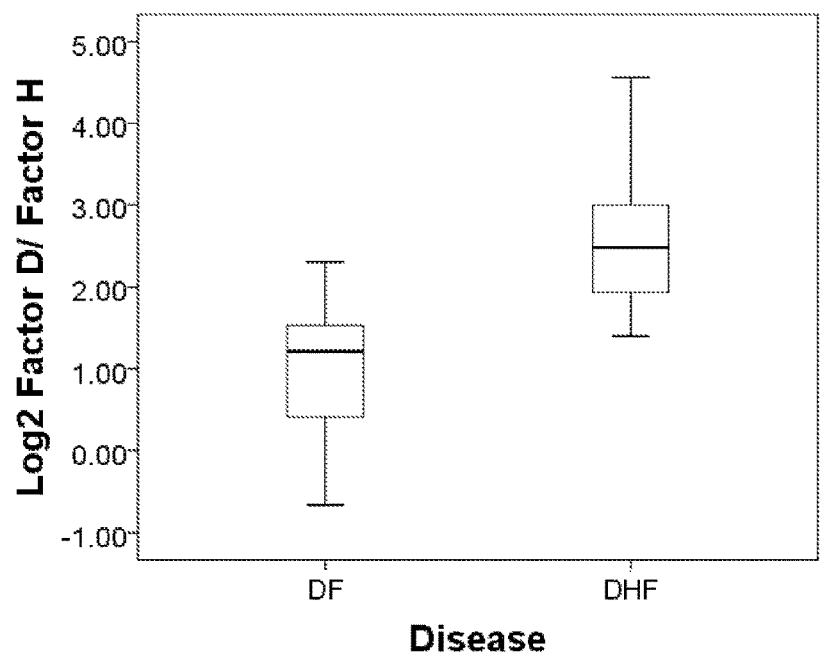
FIG. 11. Differential 2DE spot expression in dengue fever. Shown is a box-plot comparison of 2DE spot expression values for Factor D/Factor H.
Figure 12:
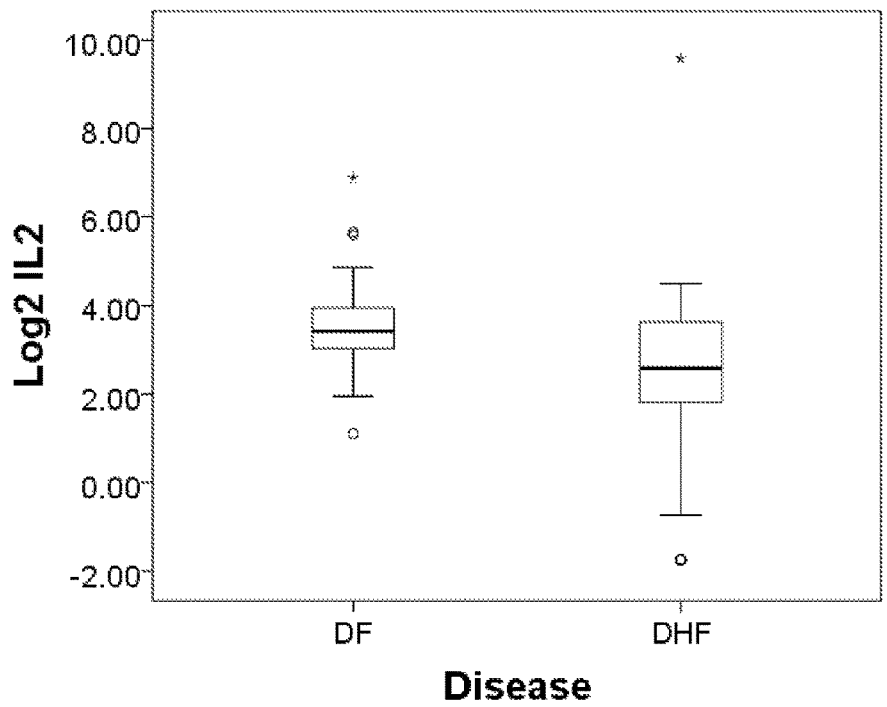
FIG. 12. Differential 2DE spot expression in dengue fever. Shown is a box-plot comparison of 2DE spot expression values IL-2.
Figure 13:
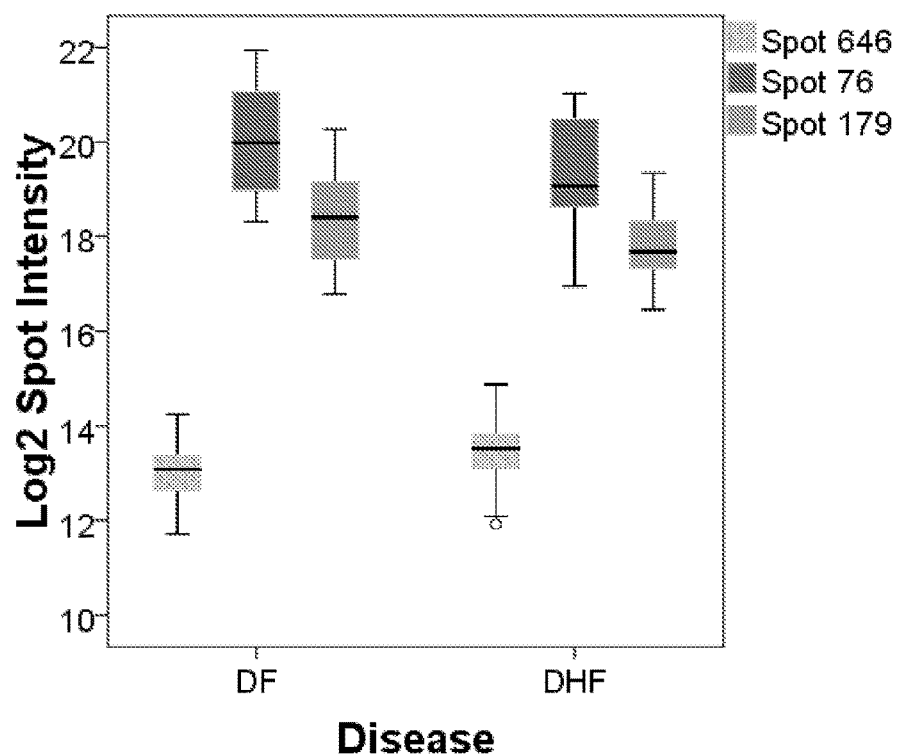
FIG. 13. Differential 2DE spot expression in dengue fever. Shown is a box-plot comparison of 2DE spot expression values for the spot intensity for spot 646, spot 76, and spot 179.

Those 121 spots, along with the 7 significant cytokines, the 5 complement factors that did not have missing data, and gender were used together to create a more complete classification model using MARS. The inventors used the log 2 transform of the data present in the modeling process, with a possible maximum of 15 basis functions and 1 possible interaction term. This resulted in a model with 100% accuracy for classifying both DF and DHF patients. The variable importance graph is shown in FIG. 8. This shows 5 variables that can be included in a classification model, with Factor D/Factor H being the most influential, and Spot 179 being the least.

Evaluation of the model performance is seen by analysis of the area under the Receiver Operating Characteristic (ROC) curve (AUC), where Sensitivity vs. 1-Specificity was plotted. In the ROC analysis, a diagonal line (45 degree slope) starting at zero indicates that the output was a random guess, whereas an ideal classifier with a high true positive rate and low false positive rate will curve positively and strongly towards the upper left quadrant of the plot. The AUC is equivalent to the probability that two cases, one chosen at random from each group, are correctly ordered by the classifier. The AUC for the DHF model is 1.000.

MARS model. The actual created model is
Y=−0.421814+0.260089*BF1+0.576361*BF3+ 0.283049*BF4+0.0991563*BF5+0.145697*BF6+ 0.427209*BF8−0.116159*BF15
  BF1=max(0, FD/FH+0.670396)
  BF3=max(0,Spot 646−13.1531)
  BF4=max(0, 13.1531−Spot 646)
  BF5=max(0, IL2−3.10266)
  BF6=max(0, 3.10266−IL2)
  BF8=max(0, 18.877−Spot 76)
  BF15=max(0, Spot 179−16.4525).

The model can be represented by the table below

TABLE 5

MARS Basis Functions.

| $B_m$ | Definition | $a_m$ | Variable descriptor |
|---|---|---|---|
| BF1 | (FD/FH + 0.67)+ | 2.60E−1 | FD/FH |
| BF3 | (DSP − 13.15)+ | 5.76E−1 | Desmoplakin |
| BF4 | (13.15 − DSP)+ | 2.83E−1 | Desmoplakin |
| BF5 | (IL2 − 3.103)+ | 0.992E−1 | IL2 |
| BF6 | (3.103 − IL2)+ | 1.46E−1 | IL2 |
| BF8 | (18.88 − Alb)+ | 4.27E−1 | Albumin* |
| BF15 | (A2M − 16.45)+ | −1.16E−1 | Alpha-2 macroglobulin |

Shown are the basis functions (BF) for the MARS model for dengue hemorrhagic fever. Bm, each individual basis function, $a_m$, coefficient of the basis function.
(y)+= max(0, y).
*Variable isoforms likely due to post-translational modification and/or proteolysis.

TABLE 6

Below is the table with spot identifications from Mass Spectrometry.

| Serial No. | Protein name | Swissprot Accession | Gel Spot No. | MS Sample No. | pI | MW (kD) | Protein Score | Abundance DHF: DF | t-test (p) |
|---|---|---|---|---|---|---|---|---|---|
| 1 | Serum albumin | P02768 | 76 | 47 | 6.26 | 250+ | 471 | −1.70 | 0.02370 |

TABLE 6-continued

Below is the table with spot identifications from Mass Spectrometry.

| Serial No. | Protein name | Swissprot Accession | Gel Spot No. | MS Sample No. | pI | MW (kD) | Protein Score | Abundance DHF:DF | t-test (p) |
|---|---|---|---|---|---|---|---|---|---|
| 2 | Alpha-2 macroglobulin | P01023 | 179 | 70 | 5.38 | 133 | 531 | −1.52 | 0.07170 |
| 5 | Desmoplakin | P15924 | 646 | 90 | 9.59 | 34 | 140 | 1.49 | 0.02660 |

Example 4

Materials and Methods

Sample Collection and Preparation. An active surveillance for Dengue diseases study was conducted in Iquitos, Peru and Maracay, Venezuela. Febrile subjects with signs and symptoms consistent with dengue virus infection were included in the study (Forshey et al., *PLoS Negl Trop Dis* 4(8):e787, 2010). On the day of presentation, a blood sample was collected for dengue virus RT-PCR confirmation and plasma preparation. Viral RNA was prepared from 140 µl sera using QIAamp Viral RNA Mini Kits following the manufacturer's instructions (QIAGEN® Inc., Valencia, Calif.). Nested dengue virus RT-PCR was performed following the protocol of Lanciotti et al. (1992) on serum samples for virus detection. The subjects were monitored for clinical outcome; DF and DHF cases were scored following WHO case definitions. An additional blood sample was collected on study day 30 for plasma preparation. Plasma specimens were stored at −70° C. until proteomic processing. Numbers of patients and disease characteristics are shown in Table 7. The initial clinical parameters were compared for the 55 volunteers (42 DF, 13 DHF) at the time of initial presentation (Table 1). Here, the number of days of fever (4.2±1 d vs 5±1 d, p<0.01), initial platelet counts (161±40.7×10$^3$/ml vs 105±33×10$^3$/ml), red blood count (4.56±13.68 vs 3±1.37) and frequency of diarrhea (46% vs 14%) were statistically different between DF and DHF, respectively (p=x).

TABLE 7

Clinical characteristics of study population.

| Phenotype | Characteristic | No. of men = 23 (42%) | No. Women = 32 (58%) | All Subjects = 55 |
|---|---|---|---|---|
| DHF (n = 13) | | N = 3 (23%) | N = 10 (77%) | N = 13 |
| | Age | 24 ± 22 | 18 ± 11 | 19 ± 13.4 |
| | Weight | 46 ± 6.6 | 42 ± 9.3 | 45 ± 14 |
| | Temp Max | 39.1 ± 1.04 | 39 ± 0.65 | 39 ± 0.70 |
| | Days Fever | 6 ± 1.73 | 5 ± 0.66 | 5 ± 1 |
| | Hemoglobin % | 12.83 ± 0.83 | 12 ± 0.97 | 12 ± 0.93 |
| | Hematocrit % | 41.16 ± 1.89 | 39 ± 3.68 | 39 ± 3.5 |
| | Platelets | 125.33 ± 13 | 99 ± 35 | 105 ± 33 |
| | RBC | 2.6 ± 0.6 | 4 ± 1.48 | 3 ± 1.37 |
| | Lymphocytes | 29.5 ± 11 | 39 ± 15.6 | 37 ± 14.8 |
| | Neutrophils | 66.1 ± 7.25 | 59 ± 14.98 | 61 ± 13.65 |
| | Diarrhea | 67% | 40% | 46% |
| DF (n = 42) | | n = 20 (47%) | n = 22 (52%) | n = 42 |
| | Age | 14.35 ± 7.05 | 16.7 ± 7.9 | 15.59 ± 7.5 |
| | Weight | 42.5 ± 17.67 | 33.4 ± 12.4 | 36 ± 13 |
| | Temp Max | 39.07 ± 0.66 | 38.72 ± 0.65 | 38.8 ± 0.67 |
| | Days Fever | 4.5 ± 1.05 | 4.08 ± 1.11 | 4.2 ± 1 |
| | Hemoglobin % | 13.96 ± 1.73 | 13.22 ± 1.32 | 13.57 ± 1.56 |
| | Hematocrit % | 42.7 ± 4.53 | 40.27 ± 4.24 | 41.42 ± 4.5 |
| | Platelets | 167.25 ± 35.7 | 155.4 ± 45 | 161 ± 40.7 |
| | RBC | 4.70 ± 1.88 | 4.46 ± 2.1 | 4.56 ± 1.98 |
| | Lymphocytes | 42.45 ± 12.25 | 48.45 ± 14.5 | 45.6 ± 13.68 |
| | Neutrophils | 56.1 ± 12.62 | 50.54 ± 14.44 | 53.19 ± 13.73 |
| | Diarrhea | 10% | 18% | 14% |

DHF, dengue hemorrhagic fever;
DF, dengue fever;
n, number;
RBC, red blood cell count;
*, p < 0.05;
§, p < 0.01;
§§, p < 0.001.

Multiplex bead-based cytokine measurements. Plasma samples were analyzed for the concentrations of 9 human cytokines (IL-6, IL-10, IFN-β, IP-10, MIP-1α, TNFα, IL-2, VEGF, and TRAIL (Bioplex, Bio-Rad, Hercules, Calif.). Plasma samples were thawed, centrifuged at 4,500 rpm for 3 minutes at 4° C., and incubated with microbeads labeled with antibodies specific to each analyte for 30 minutes. Following a wash step, the beads were incubated with the detection antibody cocktail, each bead specific to a single cytokine After another wash step, the beads were incubated with streptavidin-phycoerythrin for 10 minutes and washed again. Analyte concentrations in the sample were determined relative to standard curves of recombinant proteins using the Bioplex Manager software.

Biofluid Analysis Platform Pre-Separation Fractionation. The Biofluids Analytical Platform (BAP) pre-separation fractionation system is a semi-automated and custom-designed device consisting of four 1×30 cm columns fitted with upward flow adapters and filled with Superdex S-75 (GE Healthcare) size-exclusion beads. Samples were injected into each column through four HPLC injectors, and buffer flow was controlled by an HPLC pump (Model 305, GILSON®, Middleton, Wis.). The effluent from each column was monitored by individual UV/Vis monitors (Model 251, GILSON®, Middleton, Wis.) that each control individual fraction collectors (Model 203B, GILSON®, Middleton, Wis.). The columns were equilibrated with Running Buffer (50 mM $(NH_4)_2CO_3$, pH 8.0), and up to three hundred microliters of plasma, containing 3 mg of protein and 8 M urea spiked with 3 μg of purified Alexa-488 labeled thaumatin (Sigma-Aldrich, St. Louis, Mo.), are pumped into the columns at an upward flow rate of 20 ml/hour. The effluent was monitored at 493 nm by the UV/Vis monitor that was programmed to detect a pre-determined signal of 0.1 mV in the detector output that designated the start and end of the fluorescent thaumatin peak, and signaled the fraction collector to change collection tubes after an appropriate delay. The fractions preceding the end of the thaumatin peak were pooled and designated the "protein pool," while the fractions subsequent to the peak up to the free dye peak were pooled and designated the "peptide pool."

After size-exclusion chromatography (SEC), the protein pools were incubated at 4° C. overnight to permit further renaturation. They were then loaded onto antibody (IgY) depletion columns per the manufacturer's instructions (PHENOMENEX®, Torrance, Calif.) to deplete fourteen of the most highly abundant proteins found in plasma or serum. The flowthrough was collected and re-run through the columns a second time. The proteins obtained from the second flow-through were concentrated and resuspended in 2-DE buffer for quantitative saturation fluorescence labeling.

Saturation Fluorescence Labeling. A saturation fluorescence approach was developed using uncharged BODIPY FL-maleimide (BD) that reacts with protein thiols at a dye-to-protein thiol ratio of greater than 50:1 to give an uncharged product, with no non-specific labeling. BD-labeled protein isoelectric points are unchanged and mobilities were identical to those in the unlabeled state (Jamaluddin et al., $J$ $Virol$ 84:9533-9545, 2010; Pretzer and Wiktorowicz, $Anal.$ $Biochem.$ 374: 250-62, 2008). Using the ProExpress 2D imager (PERKINELMER®, Cambridge, UK), BD protein labeling (ex: 460/80 nm; em: 535/50 nm) has a dynamic range over 4 log orders of magnitude, and can detect 5 fmol of protein at a signal-to-noise ratio of 2:1. This saturation fluorescence labeling method has yielded high accuracy (>91%) in quantifying blinded protein samples (Turck et al., 2006. ABRF-PRG06: Relative protein quantification. In Association of Biomolecular Resource Facilities. Long Beach, C A., 2006). To ensure saturation labeling, protein extracts or pools to be labeled were analyzed for cysteine (cysteic acid) content by amino acid analysis (Model L8800, Hitachi High Technologies America, Pleasanton, Calif.) and sufficient dye added to achieve the desired excess of dye to thiol.

BD-labeled proteins were separated by 2DE (O'Farrell, $J$ $Biol$ $Chem,$ 250:4007-21, 1975), employing an IPGphor multiple sample IEF device (Pharmacia, Piscataway, N.J.) in the first dimension, and Protean Plus and Criterion Dodeca cells (Bio-Rad, Hercules, Calif.) in the second dimension. Sample aliquots were first loaded onto 11 cm dehydrated precast immobilized pH gradient (IPG) strips (Bio-Rad), and rehydrated overnight. IEF was performed at 20° C. with the following parameters: 50 Volts, 11 hours; 250 Volts, 1 hour; 500 Volts, 1 hour; 1000 Volts, 1 hour; 8000 Volts, 2 hours; 8000 Volts, 6 hour. The 1PG strips were then incubated in 4 mL of equilibration buffer (6 M urea, 2% SDS, 50 mM Tris-HCl, pH 8.8, 20% glycerol) containing 10 μl/ml tri-2 (2-carboxyethyl) phosphine (Geno Technology, Inc., St. Louis, Mo.) for 15 minutes at 22° C. with shaking. The samples were incubated in another 4 mL of equilibration Buffer with 25 mg/mL iodoacetamide for 15 min at 22° C. with shaking in order to ensure protein S-alkylation. Electrophoresis is performed at 150 V for 2.25 h, 4° C. with precast 8-16% polyacrylamide gels in Tris-glycine buffer (25 mM Tris-HCl, 192 mM glycine, 0.1% SDS, pH 8.3).

Protein Fluorescence Staining. After electrophoresis, the gels were directly imaged at 100 μm resolution using the PERKINELMER® ProXPRESS 2D Proteomic Imaging System to quantify BD-labeled proteins (>90% of human proteins contain at least one cysteine (Miseta and Csutora, $Molecular$ $Biology$ $of$ $Evolution$ 17:1232-39, 2000)). A gel containing the most common features was selected by Nonlinear Samespots software (see below) as the reference gel for the entire set of gels, and this gel was then fixed in buffer (10% methanol, 7% acetic acid in $ddH_2O$), and directly stained with SyproRuby stain (INVITROGEN™, Carlsbad, Calif.), and destained in buffer. SyproRuby is an ionic dye that typically labels proteins with multiple fluors, including a Sypro-stained gel in the analysis ensures that the maximum number of proteins can be detected and quantified. The destained gels were scanned at 555/580 nm (ex/em). The exposure time for both dyes was adjusted to achieve a value of ~55,000-63,000 pixel intensity (16-bit saturation) from the most intense protein spots on the gel.

Measurement of relative spot intensities. The 2D gel images were analyzed using Progenesis/SameSpots software (Nonlinear Dynamics, Ltd. Newcastle Upon Tyne, UK). The reference gel was selected according to quality and number of spots. Once "landmarks" were defined the program performed automatic spot detection on all images. The Sypro-Ruby stained reference gel was used to define spot boundaries, however, the gel images taken under the BD-specific filters were used to obtain the quantitative spot data. This strategy ensures that spot numbers and outlines were identical across all gels in the experiment, eliminating problems with unmatched spots (Dowsey et al., $Methods$ $Mol.$ $Biol$ 604:239-55, 2010; Karp et al., $Proteomics$ 8:948-60, 2008). Spot volumes were normalized using a software-calculated bias value assuming that the great majority of spot volumes did not change in abundance.

Protein Identification. Selected 2DE spots were picked robotically, trypsin-digested, and peptide masses identified by MALDI TOF/TOF (AB Sciex 4800, Foster City, Calif.).

Data were analyzed with the Applied Biosystems software package included 4000 Series Explorer (v. 3.6 RC1) with Oracle Database Schema Version (v. 3.19.0), Data Version (3.80.0) to acquire both MS and MS/MS spectral data. The instrument was operated in positive ion reflectron mode, mass range was 850-3000 Da, and the focus mass was set at 1700 Da. For MS data, 2000-4000 laser shots were acquired and averaged from each sample spot. Automatic external calibration was performed using a peptide mixture with reference masses 904.468, 1296.685, 1570.677, and 2465.199.

Following MALDI MS analysis, MALDI MS/MS was performed on several (5-10) abundant ions from each sample spot. A 1 kV positive ion MS/MS method was used to acquire data under post-source decay (PSD) conditions. The instrument precursor selection window was +/−3 Da. For MS/MS data, 2000 laser shots were acquired and averaged from each sample spot. Automatic external calibration was performed using reference fragment masses 175.120, 480.257, 684.347, 1056.475, and 1441.635 (from precursor mass 1570.700).

Applied Biosystems GPS Explorer™ (v. 3.6) software was used in conjunction with MASCOT to search the respective protein database using both MS and MS/MS spectral data for protein identification. Protein match probabilities were determined using expectation values and/or MASCOT protein scores. MS peak filtering included the following parameters: mass range 800 Da to 4000 Da, minimum S/N filter=10, mass exclusion list tolerance=0.5 Da, and mass exclusion list (for some trypsin and keratin-containing compounds) included masses 842.51, 870.45, 1045.56, 1179.60, 1277.71, 1475.79, and 2211.1. For MS/MS peak filtering, the minimum S/N filter=10.

For protein identification, the *Homo sapiens* taxonomy was searched in the NCBI database. Other parameters included the following: selecting the enzyme as trypsin; maximum missed cleavages=1; fixed modifications included carbamidomethyl (C) for 2-D gel analyses only; variable modifications included oxidation (M); precursor tolerance was set at 0.2 Da; MS/MS fragment tolerance was set at 0.3 Da; mass=monoisotopic; and peptide charges were only considered as +1.

Protein identification was performed using a Bayesian algorithm (Zhang and Chait, *Anal. Chem.* 72:2482-89, 2000) where matches were indicated by expectation score, an estimate of the number of matches that would be expected in that database if the matches were completely random. Confirmation of the protein identification was performed by LCMS/MS (Orbitrap Velos, ThermoFinnegan, San Jose, Calif.).

Statistical analysis. Statistical comparisons were performed using SAS®, version 9.1.3 (SAS, Inc., Cary, N.C.), PASW Statistics 17.0, Release 17.0.2, and SPSSv18 (SPSS, Inc., Chicago, Ill.).

Multivariate Analysis of Variance (MANOVA). The multivariate analysis of variance model is a popular statistical model used to determine whether significant mean differences exist among disease and gender groups. One advantage of MANOVA is that the correlation structure is taken into consideration between each cytokine. The Wilk's' lambda statistics as a MANOVA-based score were used to analyze data, when there is more than one dependent variable (SAS 9.2 PROC GLM).

Multivariate Adaptive Regression Splines (MARS). Log base 2-transformed complement factor data and gender were used for MARS modeling. The MARS model specified 15 possible basis functions and allowed only 1 interaction term. MARS is a nonparametric regression method that uses piecewise linear spline functions (basis functions) as predictors. The basis functions are combinations of independent variables and so this method allows detection of feature interactions and performs well with complex data structures (Friedman *Annals of Statistics* 19:1-67, 1991). MARS uses a two-stage process for constructing the optimal classification model. The first half of the process involves creating an overly large model by adding basis functions that represent either single variable transformations or multivariate interaction terms. The model becomes more flexible and complex as additional basis functions are added. The process is complete when a user-specified number of basis functions have been added. In the second stage, MARS deletes basis functions in order, starting with the basis function that contributes the least to the model until an optimum model is reached. By allowing the model to take on many forms as well as interactions, MARS can reliably track the very complex data structures that are often present in high-dimensional data. By doing so, MARS effectively reveals important data patterns and relationships that other models often struggle to detect. Cross-validation techniques were used within MARS to avoid over-fitting the classification model. Log-transformed cytokine and normalized spot intensities from 2DE were modeled using 10-fold cross validation and a maximum of 126 functions (Salford Systems, Inc).

Generalized Additive Models (GAM). GAMs were estimated by a backfitting algorithm within a Newton-Raphson technique. SAS®9.2 PROC GAM and STATISTICA 8.0 to fit the GAM fittings with binary logit link function that provided multiple types of smoothers with automatic selection of smoothing parameters.

What is claimed is:

1. A method for treating a subject having a dengue virus infection comprising:
   (a) measuring levels of (i) high molecular weight albumin, (ii) complement factor D and (iii) complement factor H; and determining a ratio of complement factor D to complement factor H (FactorD/FactorH) in a serum sample from the subject;
   (b) measuring levels of IL2, desmoplakin, or IL2 and desmoplakin in a serum sample from the subject;
   (c) determining with an accuracy of at least 90% by multivariate adaptive regression splines (MARS) classifier if the subject is at risk of developing dengue hemorrhagic fever (DHF) based on (i) the levels of high molecular weight albumin, (ii) the FactorD / FactorH ratio, and (iii) the levels of desmoplakin, or the levels of desmoplakin and IL2; and
   (d) treating the subject with intensive supportive care if the subject is determined to be at risk of developing DHF.

2. The method of claim 1, wherein the FactorD /FactorH ratio and level of high molecular weight albumin, desmoplakin, and IL2 are indicative of DHF.

* * * * *